US008244684B2

(12) United States Patent
Ando et al.

(10) Patent No.: US 8,244,684 B2
(45) Date of Patent: Aug. 14, 2012

(54) REPORT SEARCHING APPARATUS AND A METHOD FOR SEARCHING A REPORT

(75) Inventors: Yutaka Ando, Tokyo (JP); Osamu Kawaguchi, Tokyo (JP); Nobuhiro Tsukamoto, Tokyo (JP); Tomotaka Kasamatsu, Tokyo (JP); Hirofumi Fujii, Tokyo (JP); Hiromasa Yamagishi, Otawara (JP); Hikaru Futami, Otawara (JP); Masato Shibuya, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 734 days.

(21) Appl. No.: 12/274,782

(22) Filed: Nov. 20, 2008

(65) Prior Publication Data

US 2009/0132499 A1    May 21, 2009

(30) Foreign Application Priority Data

Nov. 21, 2007  (JP) .................................. 2007-302111

(51) Int. Cl.
*G06F 17/00* (2006.01)
(52) U.S. Cl. .................... 707/661; 707/640; 707/741
(58) Field of Classification Search .................. 707/706, 707/722, 640, 661, 741, 749, 769; 358/401; 705/3; 715/202, 273
See application file for complete search history.

(56) References Cited

U.S. PATENT DOCUMENTS

| 6,924,828 | B1 * | 8/2005 | Hirsch ........................... 715/800 |
| 7,287,221 | B2 * | 10/2007 | Bodin et al. .................. 715/202 |
| 7,315,867 | B2 * | 1/2008 | Kobayashi et al. ........... 707/749 |
| 2005/0154972 | A1 * | 7/2005 | Bodin et al. .................. 715/530 |
| 2005/0185225 | A1 * | 8/2005 | Brawn et al. .................. 358/401 |
| 2005/0251737 | A1 * | 11/2005 | Kobayashi et al. ........... 715/513 |
| 2008/0052126 | A1 * | 2/2008 | Sasai et al. ......................... 705/3 |
| 2008/0148147 | A1 * | 6/2008 | Poston et al. ................. 715/273 |
| 2008/0313130 | A1 * | 12/2008 | Hammond et al. ............... 707/2 |

(Continued)

FOREIGN PATENT DOCUMENTS

JP        2002-304467        10/2002

(Continued)

OTHER PUBLICATIONS

U.S. Appl. No. 12/821,617, filed Jun. 23, 2010, Yamagishi, et al.

(Continued)

*Primary Examiner* — Shahid Alam
(74) *Attorney, Agent, or Firm* — Oblon, Spivak, McClelland, Maier & Neustadt, L.L.P.

(57) ABSTRACT

Specified types of words are extracted from a plurality of radiology reports archived in an archive configured to archive a plurality of radiology reports. The words extracted from a single radiology report are stored in combination. In response to an input operation using an operating part of inputting the specified types of words, combinations including the specified types of words as one part are searched. A list of the specified types of words included as the other part in the searched combinations is generated. In response to an input operation using the operating part of selecting any word from the word list, a list of radiology reports including the inputted word and the selected word is generated. In response to an input operation using the operating part of selecting any report from the radiology report list, the selected radiology report is outputted from the archive to a display.

13 Claims, 19 Drawing Sheets

U.S. PATENT DOCUMENTS

2009/0132499 A1* 5/2009 Yamagishi et al. ............ 707/769
2010/0082631 A1* 4/2010 Meretab ........................ 707/741

FOREIGN PATENT DOCUMENTS

| JP | 2004-133570 | 4/2004 |
|---|---|---|
| JP | 2005-110944 | 4/2005 |
| JP | 2006-155002 | 6/2006 |
| JP | 2007-293521 | 11/2007 |

OTHER PUBLICATIONS

Japanese Office Action issued May 29, 2012, in Japanese Patent Application No. 2007-302111, filed Nov. 21, 2007.

* cited by examiner

| wb | wj | wu |
|---|---|---|
| SITE WORD | EVENT WORD | EXISTENCE WORD |
| LEFT LUNG FIELD | PLEURAL EFFUSION | RECOGNIZED |
| RIGHT LUNG FIELD | INFLAMMATION | NOT RECOGNIZED |
| ... | ... | ... |

REPORT SEARCHING APPARATUS AND A METHOD FOR SEARCHING A REPORT

BACKGROUND OF THE INVENTION

1. Field of the Invention

The present invention relates to a report searching apparatus that searches a report created in the past and a method for searching the report.

2. Description of the Related Art

Because medical practice is segmented into specialized fields, it is common to request a specialist to interpret a medical image photographed with an image diagnosis apparatus. A radiologist specialized in image interpretation displays a medical image requested for interpretation on a monitor such as a liquid crystal display or a CRT display, and summarizes the interpretation results in a radiology report.

The radiologist displays a medical image to be compared with an interpretation target image, or displays a previous radiology report involving a similar case and a diagnosed disease name, thereby using as a reference.

A radiology report created in the past is archived in an archive device including a hard disk (HD), etc. In order to read out a radiology report for reference from the archive device, for example, keyword search using an inputted search word is executed with a searching apparatus (e.g., refer to Japanese Unexamined Patent Application Publication No. 2007-293521).

When searching a radiology report including a similar case or diagnosed disease name, a conventional searching apparatus executes full-text search. Then, the searching apparatus lists all radiology reports including an inputted word as text data.

This full-text search referring to text data in radiology reports may decrease the efficiency of interpretation because it takes a substantially long search time. Further, even when the full-text search is completed after a substantial amount of time, the listed radiology reports may vary in referential value, and it is hard to distinguish which radiology reports are useful. Thus, since it is necessary to display the listed radiology reports one by one and check the contents thereof even after the search, a substantial amount of time may be wasted in finding a desired reference even after the search, and the efficiency in interpretation may be lowered. Besides, since it is difficult to find an appropriate reference from among a substantial number of listed reports, the interpreter may fail to check a radiology report that should be used as a reference actually.

SUMMARY OF THE INVENTION

An object of the present invention is provide a report searching apparatus and a method for searching a report, by which it is possible to quickly and accurately search a previous radiology report for reference.

In an aspect of the present invention: specified types of words are extracted from a plurality of radiology reports archived in an archive configured to archive a plurality of radiology reports; the words extracted from a single radiology report are stored in combination; in response to an input operation of inputting the specified types of the words by using an operating part, combinations including the inputted specified types of the words as one part thereof are searched; a list of the specified types of the words included in the searched combinations as the other part thereof is created; in response to an input operation using the operating part of selecting any word from the list of the words, a list of the radiology reports including the one word having been inputted and the other word having been selected is created; and in response to an input operation using the operating part of selecting any report from the list of the radiology reports, the selected radiology report is outputted from the archive to a display.

According to the aspect of the present invention, an operator can display a list of the words that are closely related to words inputted by the operator, and can further narrow down to desired radiology reports with the words. Consequently, it is possible to reduce the time and effort for checking the content of the radiology reports and search the desired radiology reports, and also improve the accuracy of the search.

Further, since the words closely related to the words inputted by the operator are exhibited, it becomes possible to easily consider another possibility in judgment of interpretation without overlooking.

Furthermore, since it is possible to check the relation of the name of a typical diagnosed disease with the content of a finding and the relation of the content of a finding with the name of a typical diagnosed disease, it is also possible to use for education.

DETAILED DESCRIPTION OF THE EMBODIMENTS

Figure 1:
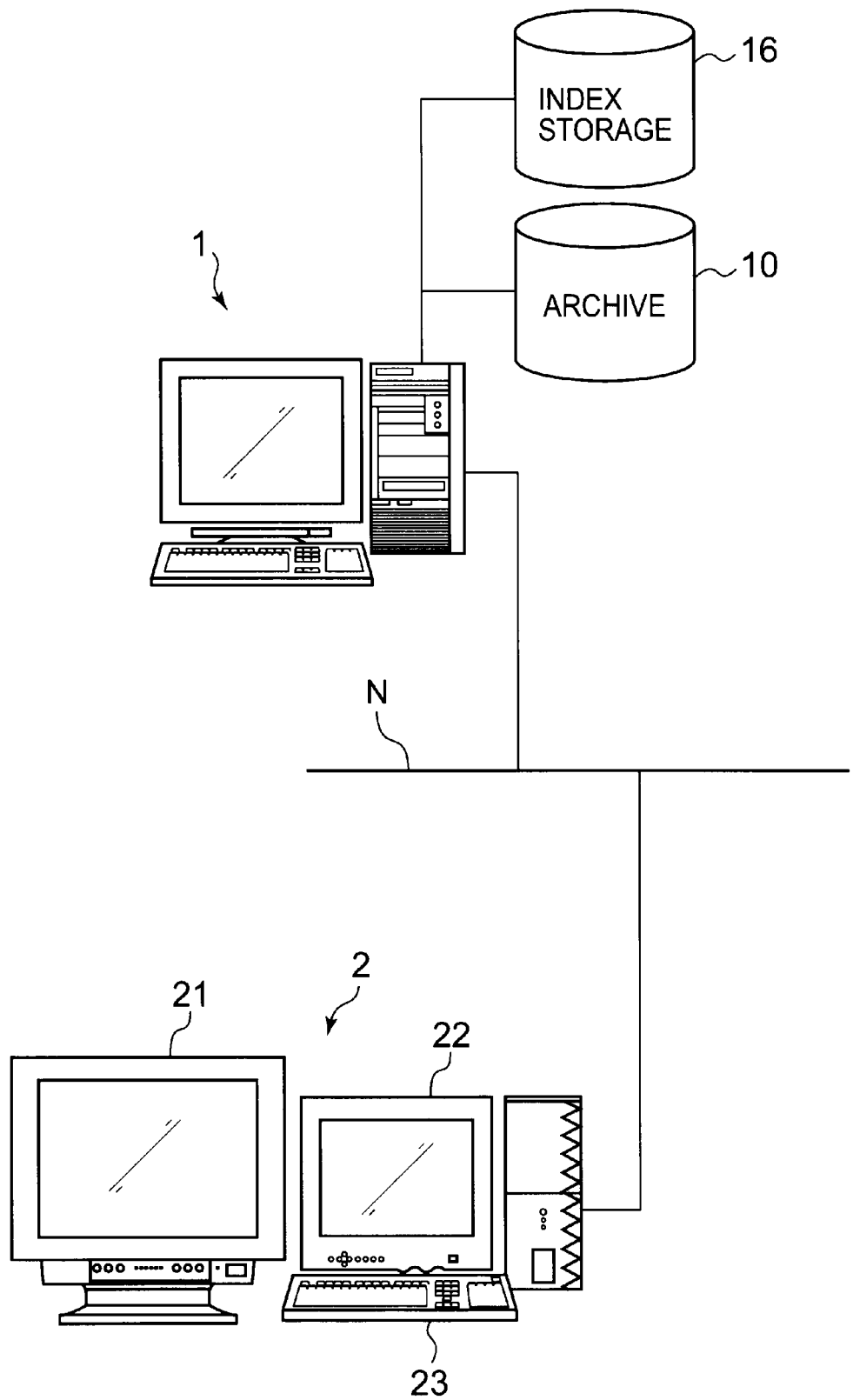
FIG. 1 shows a network including a report searching apparatus.

Referring to the drawings, a preferred embodiment of a report searching apparatus and a method for searching a report by this report searching apparatus according to the present invention will now be specifically described.

FIG. 1 is a view showing a network including a report searching apparatus 1 according to this embodiment.

The report searching apparatus 1 is connected to an interpretation terminal 2 via a network N. The network N is an electronic communication line capable of transmission of electronic data. For example, a telephone network, ISDN, FDDI, a leased line, a mobile communication network, a communication satellite line, CATV, LAN, or a combination thereof may be employed. The report searching apparatus 1 and the interpretation terminal 2 can exchange data interactively by network communication technology. Network communication technology that can be employed may include, for example, WWW (World Wide Web), TCP/IP protocol, DICOM (Digital Imaging and Communications in Medicine) protocol, etc.

The interpretation terminal 2 has a monitor 21 that displays a medical image to be interpreted, a monitor 22 that displays a radiology report input screen and a previous radiology report, and an operating part 23 such as a keyboard and a mouse.

The report searching apparatus 1 has an archive 10 such as a hard disk that archives a plurality of radiology reports created in the past, and an index storage 16 such as a hard disk that stores indexes of radiology reports archived in the archive 10. This interpretation terminal 2 sends a word, a string of words or a sentence for searching a previous radiology report in the report searching apparatus 1 to the report searching apparatus 1 as a search key. Furthermore, the interpretation terminal 2 sends, to the report searching apparatus 1, a command to request a radiology report. The report searching apparatus 1 searches in the index storage 16 by using the search key received from the interpretation terminal 2, and sends a list of search results.

Moreover, the report searching apparatus 1 reads out radiology reports corresponding to the request command from the archive 10, and sends them to the interpretation terminal 2.

Each of the report searching apparatus 1 and the interpretation terminal 2 is composed of a computer. It functions to deploy a control program stored in the hard disk into a RAM as needed, decodes the deployed control program with a CPU, and executes calculation or controls each component in accordance with the control program.

Figure 2:
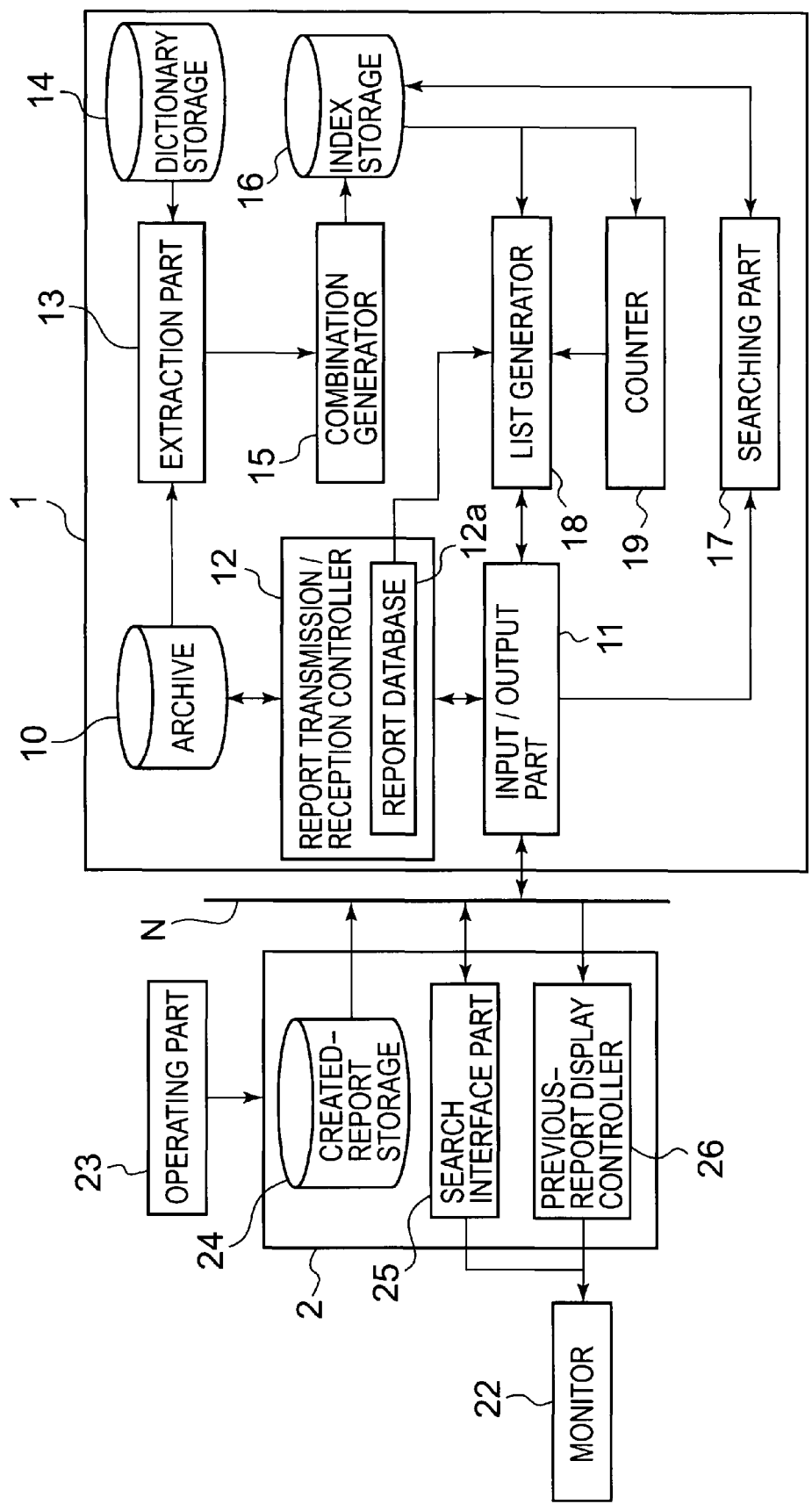
FIG. 2 shows the internal structure of a report searching apparatus and an interpretation terminal.

FIG. 2 is a block diagram showing the internal structure of the report searching apparatus 1 and interpretation terminal 2. The interpretation terminal 2 further has a created-report storage 24, a search interface part 25, and a previous-report display controller 26.

The report searching apparatus 1 further has an input/output part 11, a report transmission/receiving controller 12, an extraction part 13, a dictionary storage 14, a combination generator 15, a searching part 17, a counter 19, and a list generator 18.

The created-report storage 24 of the interpretation terminal 2 is mainly composed of a RAM and a hard disk. This created-report storage 24 stores radiology reports created by the interpretation terminal 2.

Figure 3:
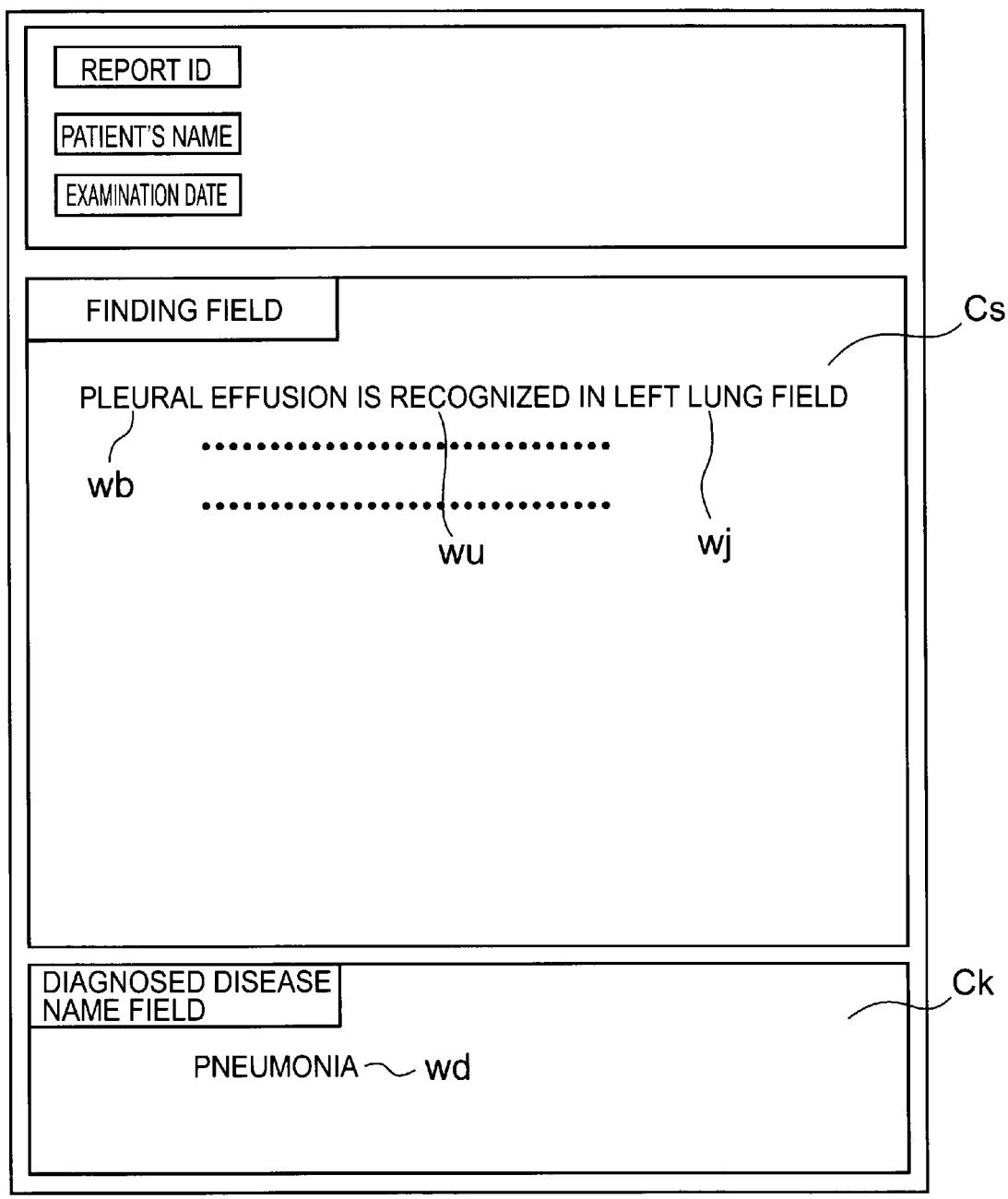
FIG. 3 shows a radiology report.

FIG. 3 is a schematic view of a radiology report stored in the created-report storage 24. The radiology report is textual data such as a document or HTML. When keys on a keyboard disposed to the operating part 23 are pressed, text data corresponding to the pressed keys is written into the radiology report. This radiology report mainly has a finding field Cs and a diagnosed disease name field Ck. In the finding field Cs, a finding representing a judgment, comment, etc., as a result of interpretation of a medical image displayed on the monitor 21 is written as text data. In the diagnosed disease name field Ck, the name of a diagnosed disease obtained from the interpretation of the medical image displayed on the monitor 21 is written as text data.

The textual data of the radiology report includes a tag that indicates the finding field Cs and a tag that indicates the diagnosed disease name field Ck. Under the tag indicating the finding field Cs, text data inputted as a finding is written. Under the tag indicating the diagnosed disease name field Ck, text data inputted as the name of a diagnosed disease is written. In general, a sentence of text data inputted in the finding field Cs is composed of a region word wb indicating a region to be commented upon, a finding word wj indicating a finding that occurred at the region, a confidence word wu indicating the positive/negative of the finding, and an auxiliary verb connecting these words. The sentence is, for example, "a pleural effusion is noted in the left lung field."

Furthermore, the text data inputted in the diagnosed disease name field Ck is a diagnosed disease name word wd such as "pneumonia." When the operator inputs one sentence composed of the region word wb, finding word wj and confidence word wu into the finding field Cs by using the operating part 23, the interpretation terminal 2 records the text data indicating the one sentence in the finding field Cs of the radiology report stored in the created-report storage 24. In the finding field Cs, a plurality of sentences may be inputted.

The search-interface part 25 is mainly composed of a CPU and a network interface. The network interface is a device such as a LAN card, a LAN board and a LAN adapter including a connector for connecting a cable of a network adapter and a line required for connecting to a network compliant with LAN standards such as Ethernet™. This search-interface part 25 sends a search key inputted with the operating part 23 or a command to request a radiology report selected with the operating part 23, to the report searching apparatus 1 via the network N.

Moreover, the search-interface part 25 causes the monitor 22 to display a search screen, receives an input event having occurred in a state where the search screen is active, and sends the inputted search word to the report searching apparatus 1 as a search key. The search-interface part 25 causes the monitor 22 to display the search screen, receives a mouse event for selecting any report from a list of radiology reports displayed on the search screen, and sends information identifying the selected radiology report and a command to request the radiology report, to the report searching apparatus 1. The information identifying a radiology report is, for example, a report ID assigned inherently to the radiology report.

Figure 4:
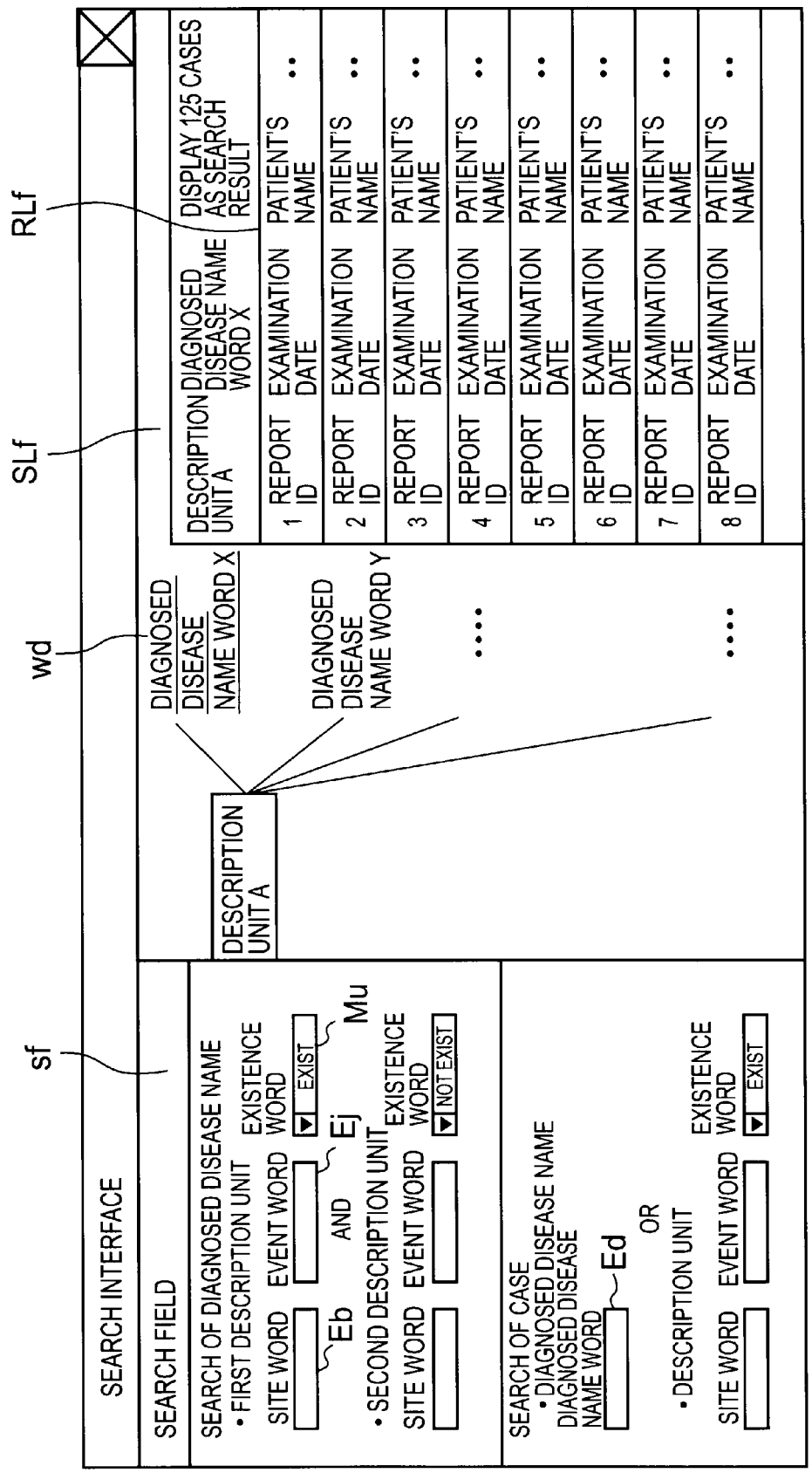
FIG. 4 shows a search screen.

FIG. 4 is a schematic view showing a search screen displayed by the search-interface part 25 on the monitor 22. The search screen is stored as GUI format data in the internal ROM of the search-interface part 25. The search-interface part 25 generates a display image from the GUI format data of the search screen, and causes the monitor 22 to display it as a search screen. The search screen has a search field Sf for inputting search words, a search-result-list field SLf for displaying a list of search results, and a report-list field RLf generated in the search-result-list field SLf. The search field Sf is composed of a region input area Eb for inputting the region word wb, an finding input area Ej for inputting the finding word wj, a confidence selection pull-down menu Mu for selecting the confidence word wu, and a disease name input area Ed for inputting the diagnosed disease name word wd. In the region input area Eb, the region word wb is inputted with the operating part 23. In the finding input area Ej, the finding word wj is inputted with the operating part 23. In the confidence selection pull-down menu Mu, a string of words indicating "positive" or "negative" is displayed and either one is selected with a mouse provided in the operating part 23.

In the disease name input area Ed, the diagnosed disease name word wd is inputted with the operating part 23.

When the region word wb and the finding word wj are inputted in the search field Sf and positive/negative of a finding is selected from the search field Sf, the search-interface part 25 sends a search command to the report searching apparatus 1 by using the inputted region word wb and finding word wj and the selected confidence word wu indicating positive/negative as a search key, which is one word-set for a single description unit. When this description unit is inputted, the search-interface part sends a search command to execute AND search of the description unit to the report searching apparatus 1. Furthermore, when receiving a list showing search results from the report searching apparatus 1, the search-interface part 25 displays a search result list in the search-result-list field SLf. In the search-result-list field SLf, for example, diagnosed disease name words wd combined with the search words in the report searching apparatus 1 are listed as described later.

This diagnosed disease name word wd is a word written in the diagnosed disease name field Ck of a previous radiology report including the search words in the finding field Cs. The operator can narrow down to more desired previous radiology reports by referring to the region word wb, finding word wj and confidence word wu inputted by himself/herself and the diagnosed disease name words wd in the list.

Upon receipt of a mouse event for selecting one of the diagnosed disease name words wd listed in this search result list from the operating part 23, the search-interface part 25 sends a command to request a list of radiology reports including the inputted region word wb, finding word wj and confidence word wu and the selected diagnosed disease name word wd, to the report searching apparatus 1. Upon receipt of the list of radiology reports from the report searching apparatus 1, the search-interface part 25 causes the report-list field RLf to display the report list. Upon receipt of a mouse event for selecting one of information identifying the radiology reports listed in this report list from the operating part 23, the search-interface part sends a command to request a radiology report including information identifying the selected radiology report, to the report searching apparatus 1.

The previous-report display controller 26 is mainly composed of a CPU and a network interface. Upon receipt of a radiology report from the report searching apparatus 1, the previous-report display controller 26 generates a display image of the received radiology report and controls the monitor 22 to display it.

The input/output part 11 of the report searching apparatus 1 is mainly composed of a network interface. This input/output part 11 receives a created radiology report, a search key, information identifying a radiology report and a request command from the report searching apparatus 1 via the network N, and sends a search result list, a report list and a radiology report to the interpretation terminal 2 via the network N. The report transmission/receiving controller 12 is mainly composed of a CPU, a network interface and a hard disk or RAM. This report transmission/receiving controller 12 controls so as to archive a radiology report sent from the interpretation terminal 2 in the archive 10, and controls so as to send a radiology report archived in the archive 10 to the interpretation terminal 2. When the input/output part 11 receives a radiology report, the report transmission/receiving controller 12 registers the received radiology report into the report database 12*a* and archives it into the archive 10. The report database 12*a* is stored in the hard disk, and a path, which represents information identifying a radiology report newly sent to the report database 12*a*, an examination date, patient name, etc., included in the radiology report and an archive destination of the report, is written therein.

Furthermore, when the input/output part 11 receives a request command including information identifying a radiology report from the interpretation terminal 2, the report transmission/receiving controller 12 refers to the report database 12*a*, reads out a path paired with the sent radiology report identifying information, and controls the input/output part 11 to send a radiology report archived in an archive destination represented by the path.

The extraction part 13 is mainly composed of a CPU. The dictionary storage 14 is mainly composed of a hard disk or RAM.

The combination generator 15 is mainly composed of a CPU.

The extraction part 13, the dictionary storage 14, and the combination generator 15 create indexes for searching radiology reports archived in the archive 10, and store them into the index storage 16.

Figure 5:
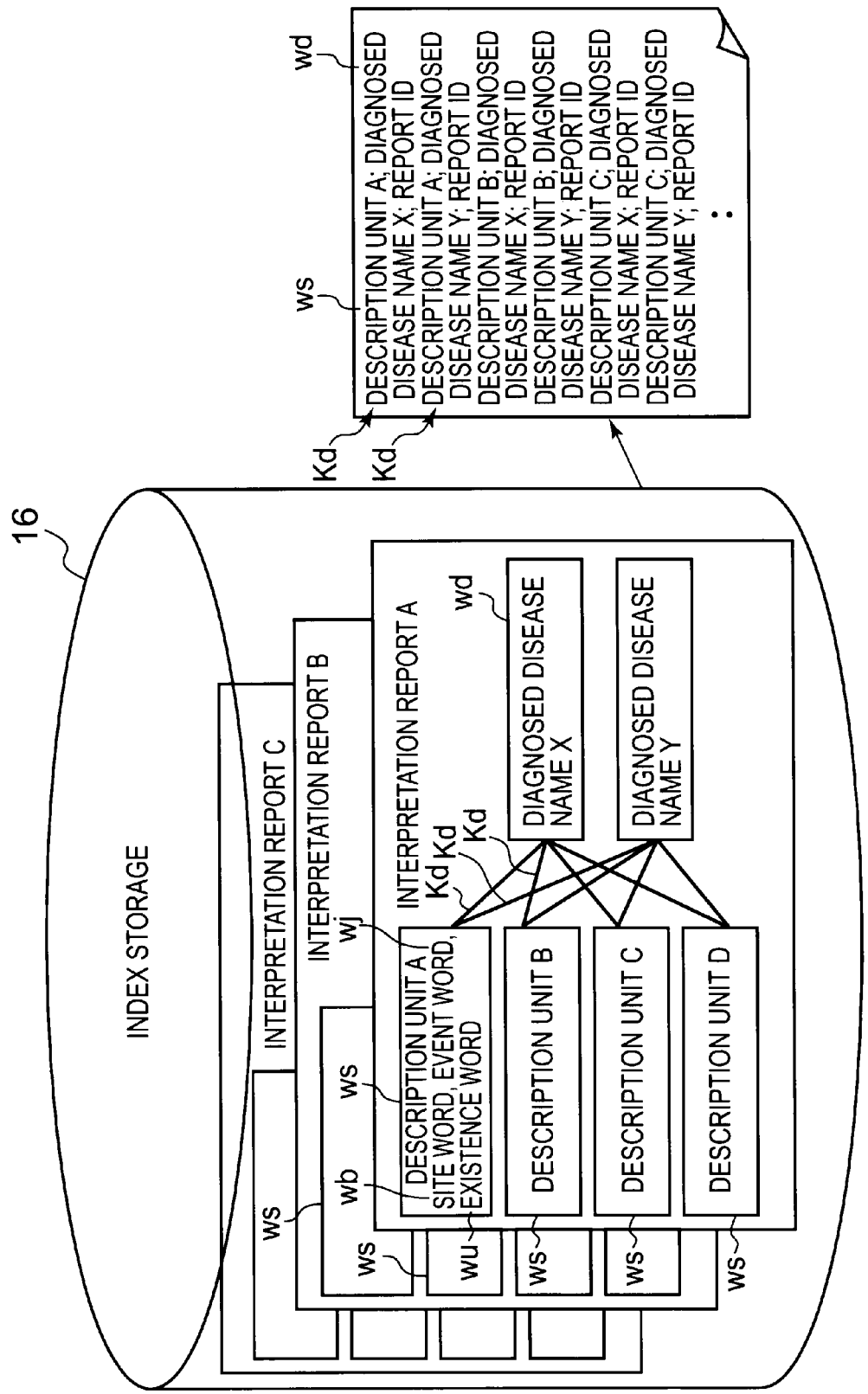
FIG. 5 shows the data structure of an index stored in an index storage.

FIG. 5 is a data configuration view showing indexes stored in the index storage 16. The index is data that links combination data Kd of words included in each radiology report stored in the archive 10 with a report ID of the radiology report including the combination of words.

The index storage 16 stores combination data of a word-set of each of the description units (hereinafter referred to as "description unit data ws") written in the finding field Cs of a single radiology report with the diagnosed disease name word wd indicating the name of a diagnosed disease in the diagnosed disease name field Ck of the radiology report.

The description unit data ws is a set of data composed of the region word wb, finding word wj and confidence word wu for each sentence among words in the finding field Cs of a radiology report. For example, in a case where sentences A, B, C and D are written in the finding field Cs and a diagnosed disease name word wd of X and a diagnosed disease name word wd of Y are written in the diagnosed disease name field Ck in a radiology report A, eight kinds of combination data Kd are generated in total from this radiology report A and stored into the index storage 16. The eight kinds of combination data Kd are generated by pairing and combining one of description unit data ws of A composed of the region word wb, finding word wj and confidence word wu as one set forming the sentence A, similarly composed description unit data ws of B, similarly composed description unit data ws of C and similarly composed description unit data ws of D, with one of the diagnosed disease name word wd of X and the diagnosed disease name word wd of Y.

The combination data Kd in which the description unit data ws is combined with the diagnosed disease name word wd is generated for each radiology report stored in the archive 10, and then stored into the index storage 16 regardless of duplication.

"Regardless of duplication" is that, if a plurality of radiology reports that includes a sentence including the same region word wb, finding word wj and confidence word wu and the same diagnosed disease name word wd are archived, a plurality of the same combination data Kd in which the same words are combined exist in the index storage 16. For example, if "left lung field," "pleural effusion" and "positive" are written in one sentence in the finding field Cs and "pneumonia" is written in the diagnosed disease name field Ck in a radiology report A, as well as if "left lung field," "pleural effusion" and "positive" are written in one sentence in the finding field Cs and "pneumonia" is written in the diagnosed disease name field Ck in a radiology report B, combination data Kd containing the description unit data ws of the word set "left lung field," "pleural effusion" and "positive" and the diagnosed disease name word wd "pneumonia" will be found at least twice in the index storage 16. A difference between the two means whether the report ID of the radiology report A or the report ID of the radiology report B is linked.

In the index-creation process described above, the extraction part 13 executes a structuring process of dividing a radiology report on the word-by-word basis and restructuring each sentence into description unit data ws in which the region word wb, finding word wj and confidence word wu are formed in one set. To be specific, the extraction part 13 extracts words from each sentence in the finding field Cs and extracts the diagnosed disease name word wd from the diagnosed disease name field Ck in a radiology report.

Subsequently, the extraction part creates, for every sentence, the description unit data ws formed by the words extracted from one sentence as one set. The dictionary storage 14 stores dictionary data in which various words are registered. The extraction part 13 searches the words recorded in the dictionary data in each sentence of the radiology report.

The combination generator 15 generates a combination of the description unit data ws and the diagnosed disease name word wd created from a single radiology report, and stores the combination linked with a report ID into the index storage 16.

Figure 6:
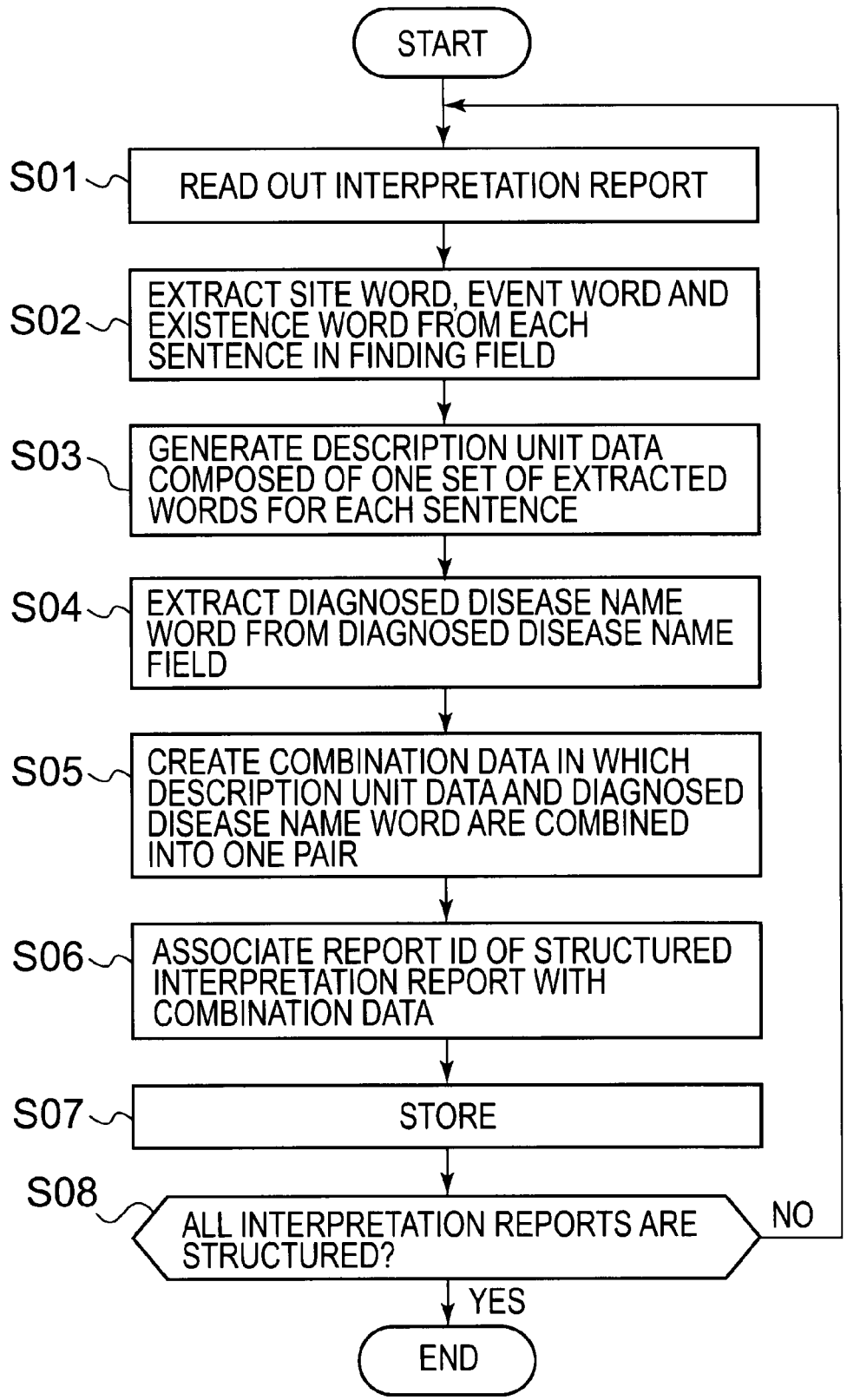
FIG. 6 is a flowchart showing an example of a process for creating an index.

FIG. 6 is a flowchart showing an example of a process in which the extraction part 13, the dictionary storage 14 and the combination generator 15 create an index. Firstly, the extraction part 13 reads out a radiology report from the archive 10 (S01).

When the input/output part 11 receives the radiology report from the interpretation terminal 2 and the report transmission/receiving controller 12 registers the received radiology report into the report database 12*a* and archives it into the archive 10, the extraction part 13 reads out the archived radiology report to create an index.

Referring to the dictionary data, the extraction part 13 extracts the region word wb, finding word wj and confidence word wu from each sentence in the finding field Cs of the read-out radiology report (S02), and generates the description unit data ws including the extracted words as one set for each sentence (S03).

Figures 7, 8:
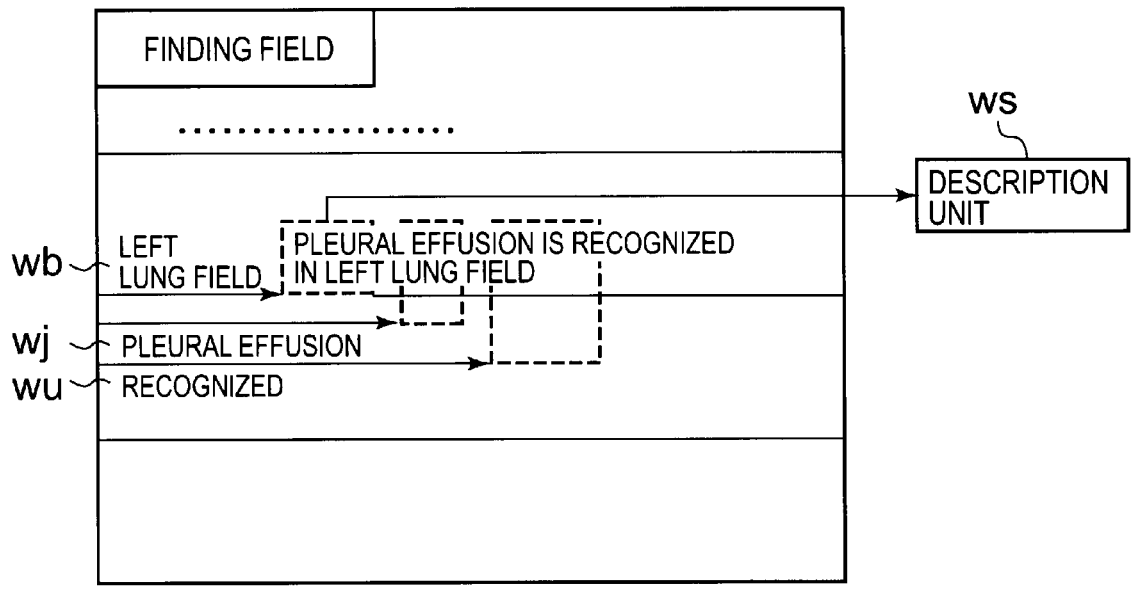
FIG. 7 shows the data structure of the dictionary data.
FIG. 8 shows an aspect of extraction.

FIG. 7 is a data structure view showing the dictionary data stored in the dictionary storage 14. Furthermore, FIG. 8 is a schematic view showing an aspect of extraction by the extraction part 13.

When extracting words, the extraction part 13 refers to the dictionary data to specify words to be extracted. The dictionary data is stored in the dictionary storage 14. As shown in FIG. 7, a number of words belonging to the region words wb, a number of words belonging to the finding words wj, and a number of words belonging to the confidence words wu are recorded in the dictionary data. As shown in FIG. 8, the extraction part 13 reads out an $N^{th}$ (N=1, 2, 3 . . . ) sentence in the finding field Cs of a radiology report, and executes matching with each of the words stored in the dictionary data while sequentially moving a matching position from the beginning to the end of the data of the read-out sentence. When a matched word is included in the sentence, the word is recorded so as to be included in the description unit data ws for the scanned sentence. By executing matching with each of the words recorded in the dictionary data, the region word wb, finding word wj and confidence word wu are matched from one sentence, and are recorded as one set into the description unit data ws. The extraction part 13 repeats this extraction process from the first sentence to the last sentence written in the finding field Cs of the radiology report, and creates the description unit data ws corresponding to each of the sentences.

Next, the extraction part 13 extracts the diagnosed disease name word wd from the diagnosed disease name field Ck (S04). If there are a plurality of diagnosed disease name words wd in the diagnosed disease name field Ck, all of the diagnosed disease name words wd are extracted.

Figure 9:
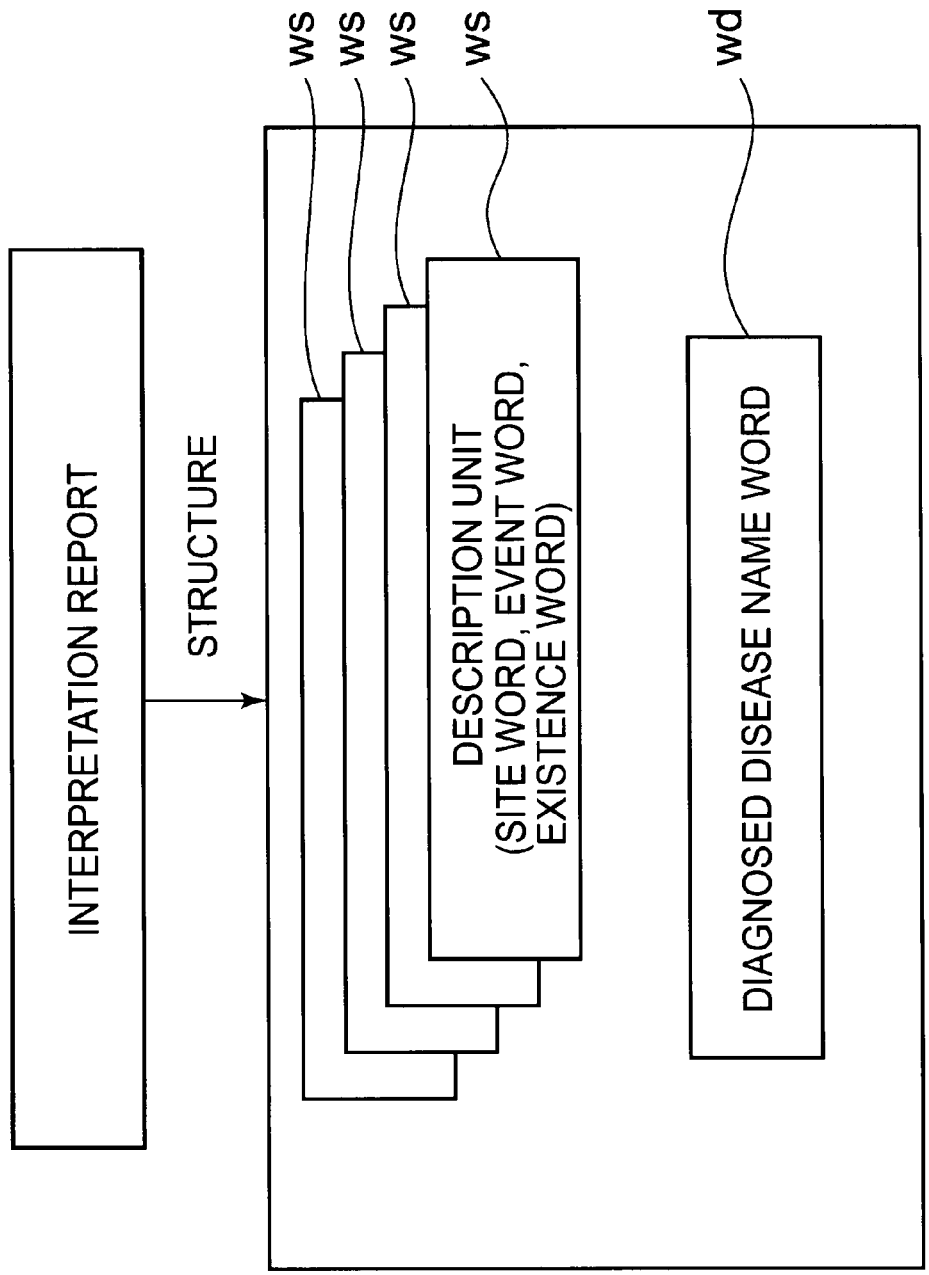
FIG. 9 shows radiology report information structured by the extraction process.

FIG. 9 is a schematic view showing radiology report information structured by the extraction process. As shown in FIG. 9, the radiology report is structured into the description unit data ws of each sentence written in the finding field Cs and the diagnosed disease name word wd by the process of this extraction part 13.

Figure 10:
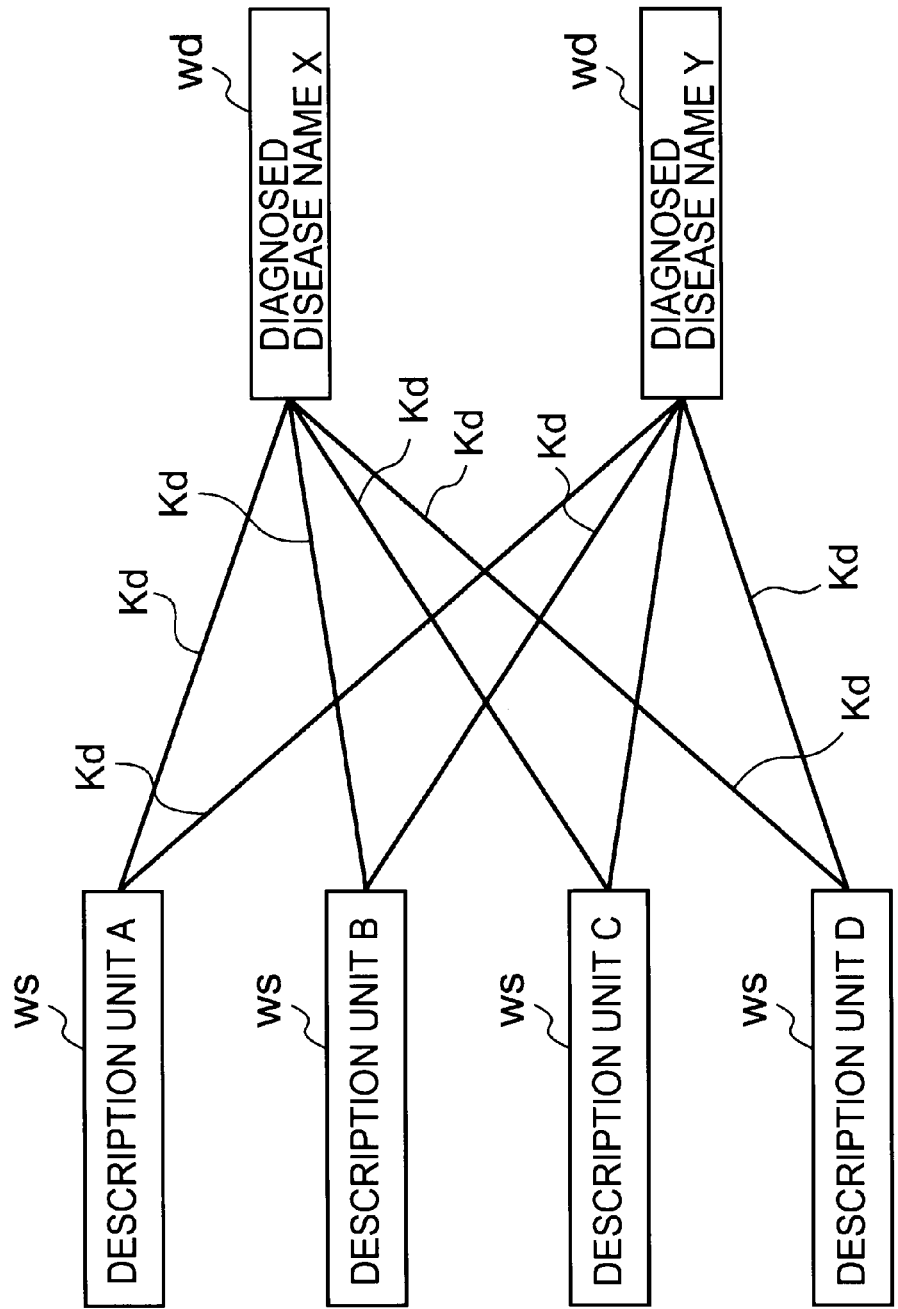
FIG. 10 shows an example of a combination process.

Next, when one radiology report is structured by the extraction part 13, the combination generator 15 creates the combination data Kd in which one of the description unit data ws is paired with one of the diagnosed disease name words wd (S05). FIG. 10 is a schematic view showing an example of this combination process. When one radiology report is structured into the description unit data ws of A, B, C, D and the diagnosed disease name words wd of X, Y by the process of the extraction part 13, the combination generator 15 generates the combination data Kd by forming pairs in all combinations of the description unit data ws of A, B, C, D as word-sets of each sentence in the finding field Cs with the diagnosed disease name words wd of X, Y as words in the diagnosed disease name field Ck, in a manner that the description unit data ws of A is combined with the diagnosed disease name word wd of X, the description unit data ws of A is combined with the diagnosed disease name word wd of Y, the description unit data ws of B is combined with the diagnosed disease name word wd of X, and the description unit data ws of B is combined with the diagnosed disease name word wd of Y.

Then, after creating the combination data Kd, the combination generator 15 links a report ID identifying the structured radiology report with each of the combination data Kd (S06) and stores into the index storage 16 (S07). Then, if all of the radiology reports stored in the index storage 16 are not structured (S08, No), the process in S01 to S07 is repeated on the remaining radiology reports.

The report searching apparatus 1 searches radiology reports by using the combination data Kd of each of the radiology reports created by the extraction part 13, dictionary storage 14 and combination generator 15, generates a search result list and a report list to send to the interpretation terminal 2, and further sends the radiology reports to the interpretation terminal 2. The searching process executed in the report searching apparatus 1 is executed by the searching part 17, the counter 19, and the list generator 18. The searching part 17 is mainly composed of a CPU. The counter 19 is mainly composed of a CPU. The list generator 18 is mainly composed of a CPU.

By using the words received as a search key from the interpretation terminal 2, the searching part 17 searches combination data kd including these words as a description unit from the index storage 16.

With the searched combination data Kd as a parameter, the counter 19 counts the number of the combination data kd that include the same diagnosed disease name word wd for every diagnosed disease name word wd included in the combination data kd. Specifically, the counter counts the number of radiology reports in which a sentence composed of the same region word wb, finding word wj and confidence word wu is written in the finding field Cs and the same diagnosed disease name word wd is written in the diagnosed disease name field Ck.

The list generator 18 generates a list of the diagnosed disease name words wd included in the searched combination data Kd as a search result list. At the time of creation of the list of the diagnosed disease name words wd, the list generator 18 records the number of the combination data kd including the same diagnosed disease name word wd counted and obtained by the counter 19, i.e., the number of radiology reports including the same sentence and the same diagnosed disease name, by linking for every diagnosed disease name word wd.

Furthermore, the list generator 18 generates a list of radiology reports that include the diagnosed disease name word wd selected from the list of diagnosed disease name words wd and a word-set of the description unit sent as a search key.

Figure 11:
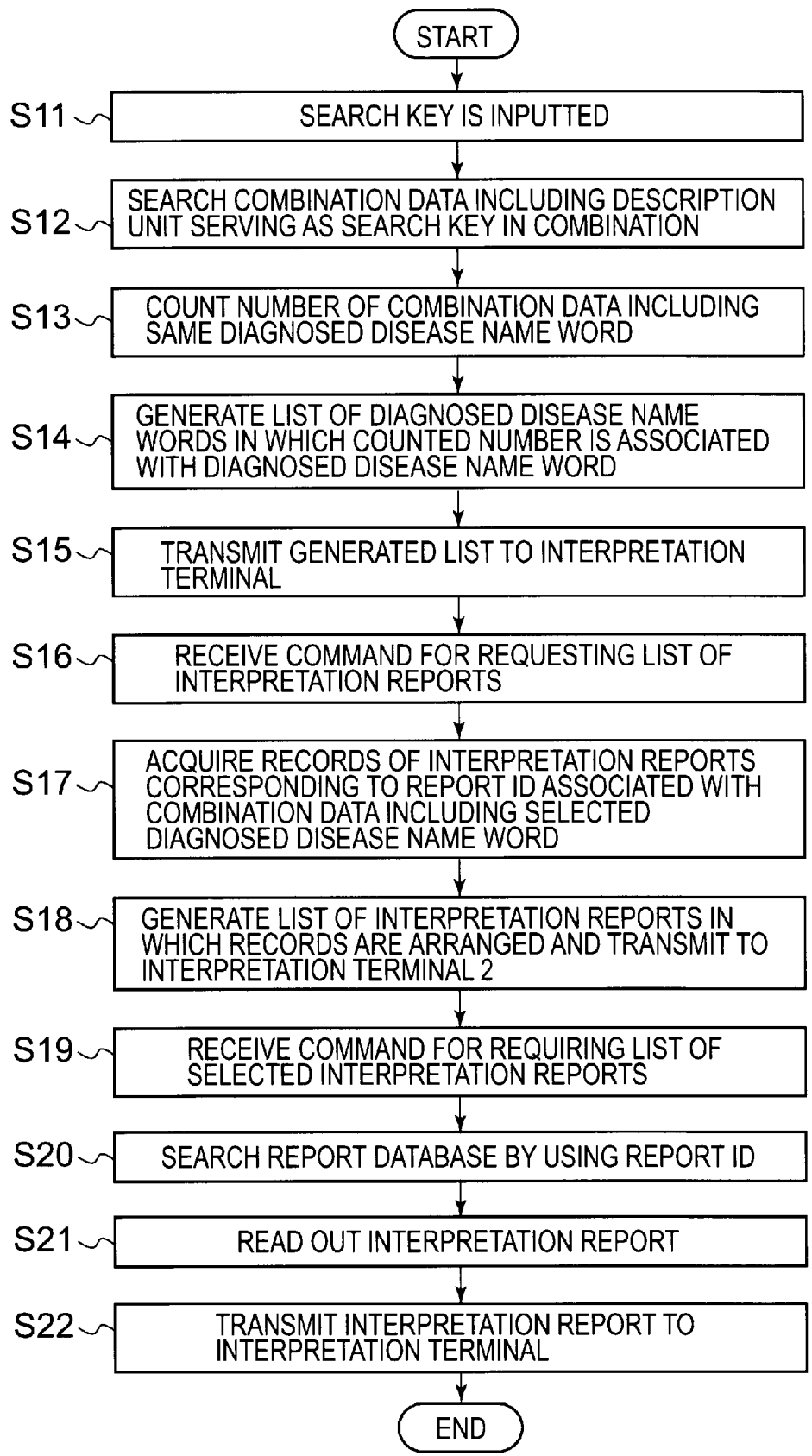
FIG. 11 is a flowchart showing an example of a searching process.
Figure 12:
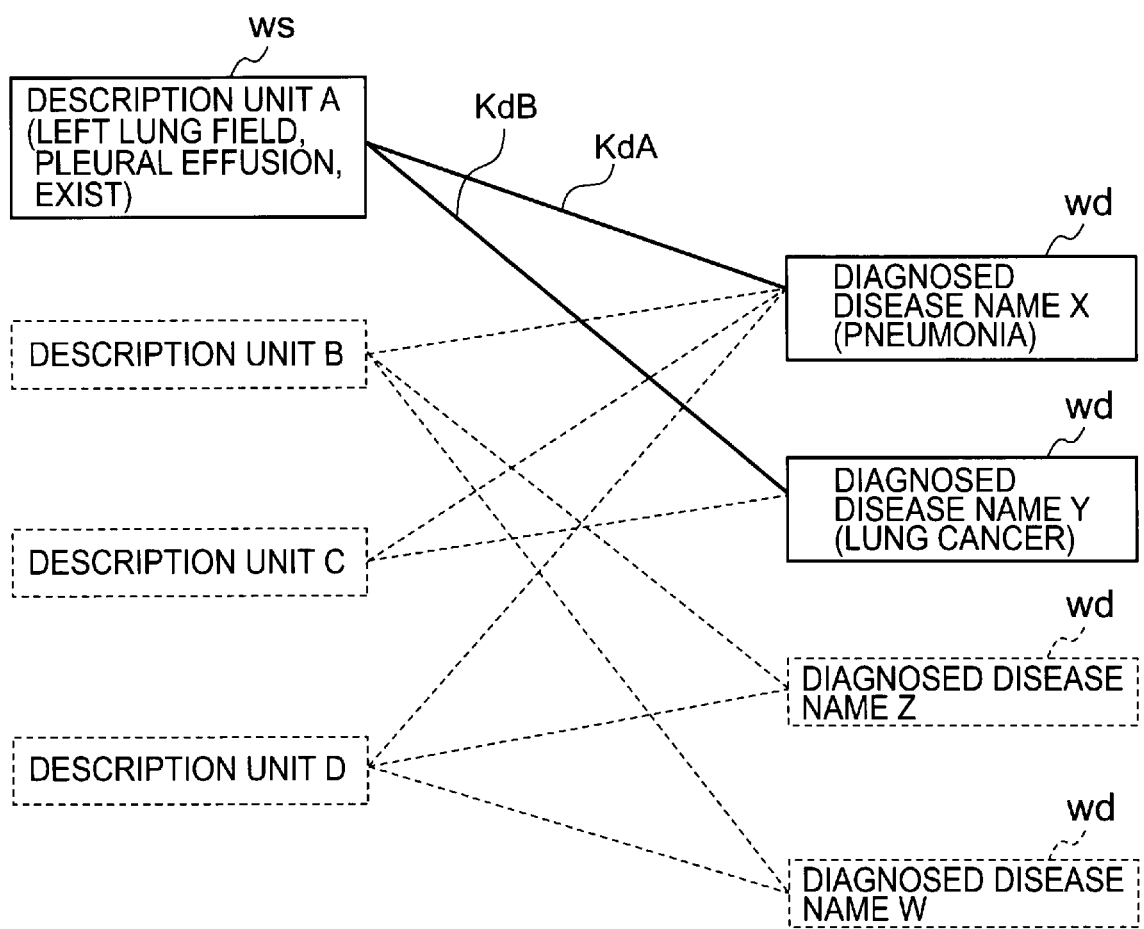
FIG. 12 shows a specific example of search.

FIG. 11 is a flowchart showing an example of a searching process performed by the searching part 17, the counter 19, and the list generator 18. Firstly, when a search key is inputted by the interpretation terminal 2 (S11), the searching part 17 searches combination data kd including a description unit to become a search key from the index storage 16 (S12). The search key is composed of a word-set including the region word wb, finding word wj and confidence word wu. The searching part 17 searches combination data kd including the description unit data ws composed of the word-set from the index storage 16. FIG. 12 is a schematic diagram showing a specific example of this search. For example, when a search key including "left lung field" as the region word wb, "pleural effusion" as the finding word wj, and "positive" as the confidence word wu is received, a plurality of combination data kdA and a plurality of combination data kdB are specified. The combination data kdA include the description unit data ws composed of a word-set of "left lung field," "pleural effusion" and "exist" and "pneumonia." The combination data kdB include the description unit data ws composed of a word-set of "left lung field," "pleural effusion" and "exist" and "lung cancer." The searching part 17 flags each of the specified combination data KdA and each of the specified combination data KdB.

When the searching part 17 searches combination data kd, the counter 19 sets the searched combination data kd as a parameter and counts the number of combination data kd that include the same diagnosed disease name word wd for every diagnosed disease name word wd (S13). The counter 19 firstly extracts all diagnosed disease name words wd included in the flagged combination data kd.

For example, "pneumonia" included in the combination data kdA, and "lung cancer" included in the combination data kdB are extracted.

Then, the number of the combination data kdA that include the diagnosed disease name word wd indicating "pneumonia" is counted from the flagged combination data. Also, the number of the combination data KdB that include the diagnosed disease name word wd indicating "lung cancer" is counted.

Figure 13:
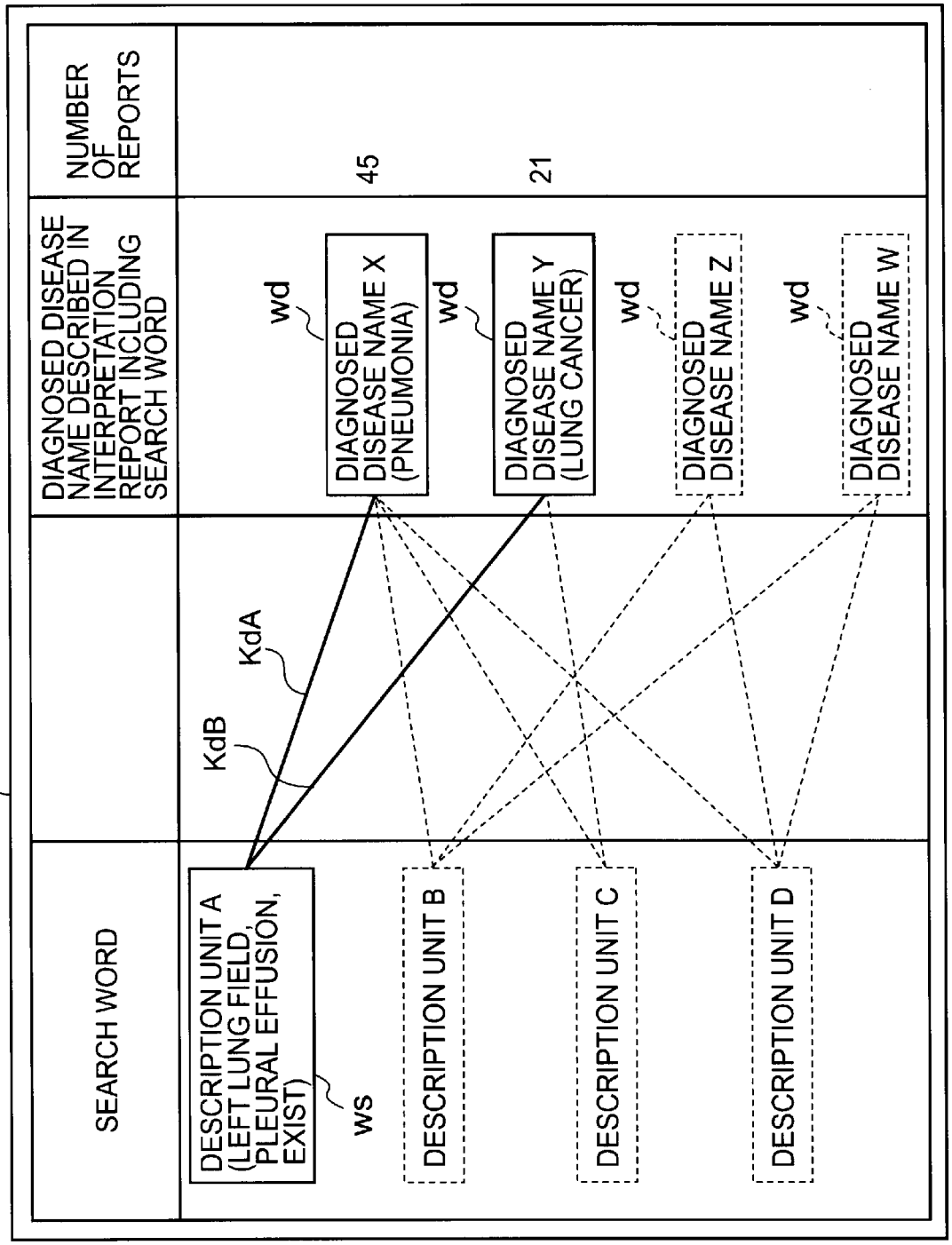
FIG. 13 shows a list of search results.

FIG. 13 is a schematic view showing a list of search results.

After the search by the searching part 17 and counting by the counter 19, as shown in FIG. 13, the list generator 18 generates a list in which each diagnosed disease name word wd included in the combination data kd specified by the searching part 17 is linked with the counted number as the number of reports (S14). Then, the list generator 18 sends the generated list to the interpretation terminal 2 via the input/output part 11 and the network N (S15).

The sent list is displayed in the search-result-list field SLf on the search screen of the monitor 22 of the interpretation terminal. When the operator selects one diagnosed disease name word wd from this list by using the operating part 23, a command to request a list of radiology reports that further include the selected diagnosed disease name word wd is sent from the interpretation terminal 2 to the report searching apparatus 1. Upon receipt of the command to request the list of the radiology reports that further include the selected diagnosed disease name word wd (S16), the list generator 18 searches in the report database 12a by using a report ID linked with combination data kd that include the selected diagnosed disease name word wd among the searched combination data kd as a search key, and acquires records of the relevant radiology reports (S17). Then, the list generator generates a list in which the records of the radiology reports are listed, and sends the list to the interpretation terminal 2 via the input/output part 11 and the network N (S18). For example, when "pneumonia" included in the combination data kdA is selected on the interpretation terminal 2, the report searching apparatus 1 generates a list of radiology reports including "left lung field," "pleural effusion" and "positive" in the finding field Cs, and "pneumonia" in the diagnosed disease name field Ck, based on the report IDs linked with the combination data kdA. The sent list is displayed in the report-list field RLf on the search screen of the monitor 22 of the interpretation terminal. When the operator selects one radiology report from this list by using the operating part 23, a command to request a list of the selected radiology reports is sent from the interpretation terminal 2 to the report searching apparatus 1.

Upon receipt of the command to request the list of the selected radiology reports (S19), the report transmission/receiving controller 12 searches in the report database 12a by using a report ID included in the command (S20), reads out radiology reports from the archive area of the archive 10 indicated by a path recorded in the relevant record (S21), and sends them to the interpretation terminal 2 via the input/output part 11 and the network N (S22).

In the interpretation terminal 2, the received radiology reports are displayed on the monitor 22 by the previous-report display controller 26.

In this way, in the report searching apparatus 1 according to this embodiment, combination data kd in which words in the finding field Cs such as a word-set of a description unit with words in the diagnosed disease name field Ck included in the radiology reports are previously generated as indexes, and when a word-set of a description unit is inputted as a search key, firstly, a list of words in the diagnosed disease name field Ck combined with this word-set is generated. Accordingly, the operator can know words in the diagnosed disease name field Ck closely related to the words in the finding field Cs inputted by himself/herself, and can narrow down to a more desired radiology report based on the words in the diagnosed disease name field Ck. Moreover, because the number of radiology reports that include the inputted word-set in the description unit and the words in the diagnosed disease name field Ck is displayed in the list of words in the diagnosed disease name field Ck, this number can be used as a degree of relevance between the words in the finding field Cs inputted by themselves and the words in the diagnosed disease name field Ck, thereby making it possible to narrow down the results to radiology reports having a high referential value.

Figure 14:
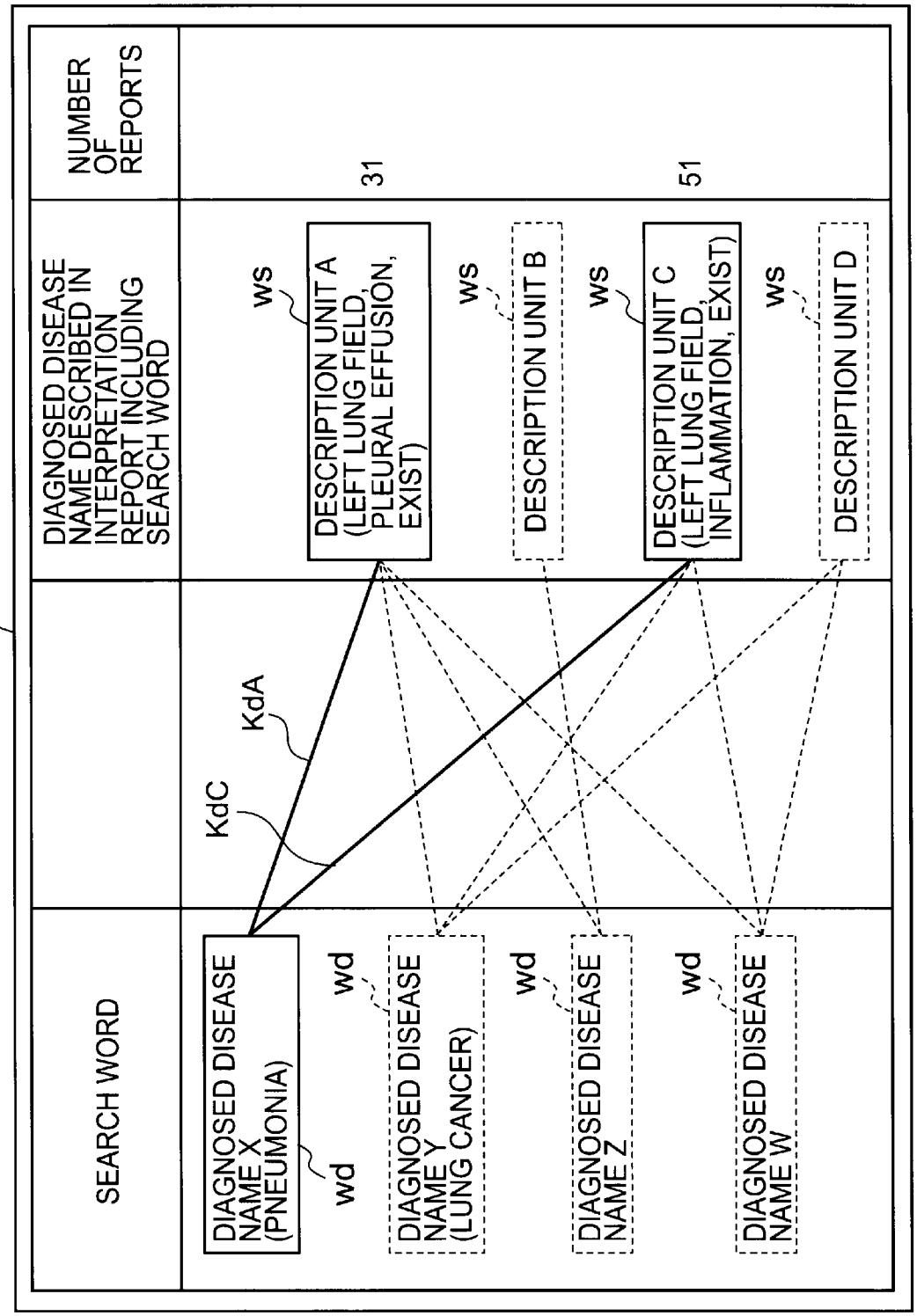
FIG. 14 shows a searching example when a diagnosed disease name word is inputted as a search key.

Next, another search example with the combination data kd combining a word in the finding field Cs and a word in the diagnosed disease name field Ck as an index will be explained. In this search example, a word in the diagnosed disease name field Ck is inputted as a search key. The search-interface part 25 of the interpretation terminal 2 displays a not-shown input field of the diagnosed disease name word wd in the search field Sf. FIG. 14 is a schematic view showing a search example in which the diagnosed disease name word wd is inputted as a search key. For example, when receiving a search key including "pneumonia" as the diagnosed disease name word wd, the searching part 17 specifies data KdA and KdC that include the "pneumonia." When the searching part 17 specifies the combination data kdA and KdC, the counter 19 counts the numbers of the combination data kdA and the the combination data kdC. Then, a list of the results from the search and counting is created and sent to the interpretation terminal 2. The sent list is displayed in the search-result-list field SLf in the search screen of the monitor 22 of the interpretation terminal. When the operator selects one description unit, e.g., a description unit A, from this list by using the operating part 23, a command to request a list of radiology reports that further include the selected description unit data ws of A is sent from the interpretation terminal 2 to the report searching apparatus 1.

The list generator 18 reads out the report ID linked with the combination data kd that are flagged and that include the selected description unit data ws of A, searches in the report database 12a by using the read-out report ID as a search key, and acquires the records of the relevant radiology reports. Then, the list generator generates a list in which the records of the radiology reports are listed, and sends to the interpretation terminal 2 via the input/output part 11 and the network N.

The sent list is displayed in the report-list field RLf in the search screen of the monitor 22 of the interpretation terminal.

Thus, in the report searching apparatus 1 according to this embodiment, by previously generating the combination data kd that combines words in the finding field Cs such as a word-set of a description unit included in radiology reports, with words in the diagnosed disease name field Ck, as indexes, even when a diagnosed disease name is inputted as a search key, it is possible to generate a list of words in the finding field combined with the diagnosed disease name.

Accordingly, the operator can know a finding closely related with the diagnosed disease name inputted by him/her, and can further narrow down to desired radiology reports by using a word representing the finding.

Figure 15:
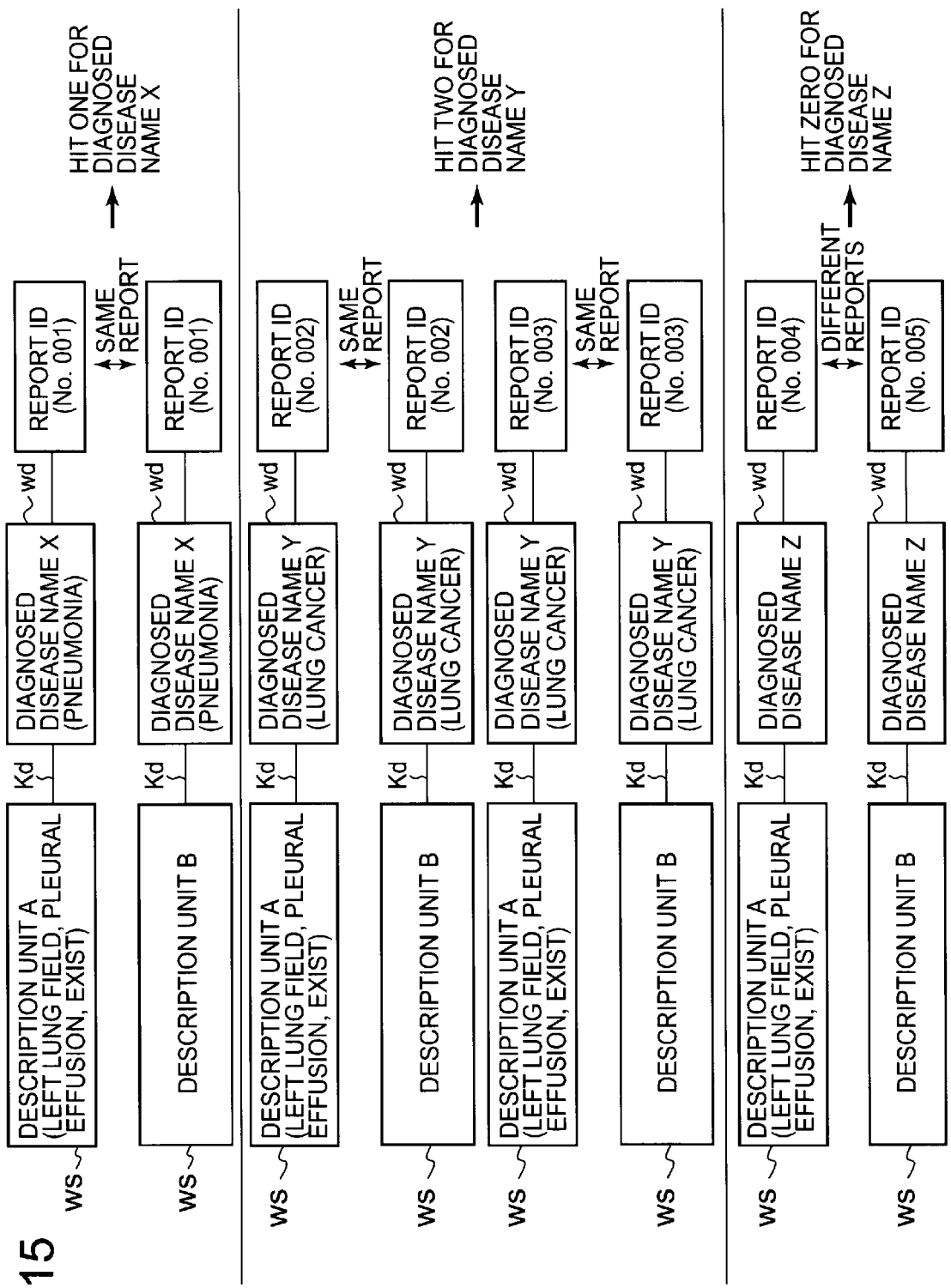
FIG. 15 shows a searching example when a plurality of description units are inputted as a search key.

Next, another search example using an index that links the combination data kd combining words in the finding field Cs and words in the diagnosed disease name field Ck, with report IDs, will be explained. In this search example, AND search is executed on a plurality of description units in the finding field Cs. The search-interface part 25 of the interpretation terminal 2 displays plural units of region input areas Eb, finding input areas Ej and confidence selection pull-down menus Mu in the search field Sf. FIG. 15 is a schematic view showing a search example when a plurality of description units are inputted as search keys. When a description unit A and a description unit B are inputted as search keys, the searching part 17 searches radiology reports in which the description unit A and the description unit B are written in the finding field Cs by using the combination data kd and the report IDs, the list generator 18 generates a list of diagnosed disease name words written in the diagnosed disease name field Ck of the searched radiology reports by using flags attached by the searching part 17, and the counter 19 counts the number of the radiology reports searched by using the combination data kd and the report IDs, for every diagnosed disease name word wd.

Consequently, a list of the diagnosed disease name words wd written in the finding fields of the radiology reports including the description unit A and the description unit B in the finding field Cs is generated, and then it becomes possible, by selecting the diagnosed disease name word wd, to represent a list of radiology reports including the description unit A and the description unit B in the finding field Cs and also including the selected diagnosed disease name word wd in the diagnosed disease name field Ck by using the combination data Kd.

Figure 16:
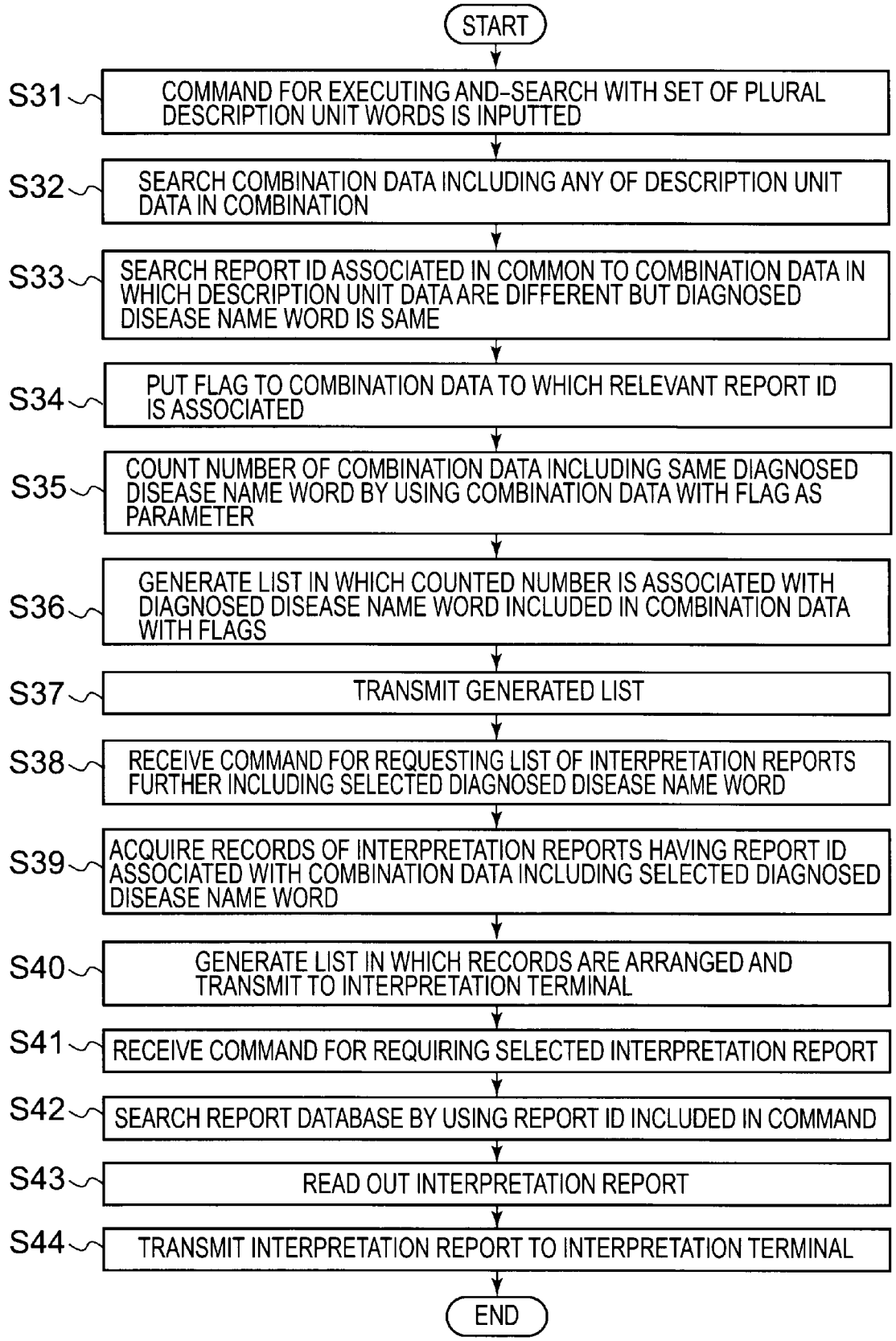
FIG. 16 is a flowchart showing a searching process when a plurality of description units are inputted as a search key.

FIG. 16 is a flowchart showing the searching process when a plurality of description units are inputted as search keys. Firstly, when a command to execute AND search with word-sets of a plurality of description units is inputted from the interpretation terminal 2 (S31), the searching part 17 searches the combination data kd including any of the inputted description unit data ws in the combinations, from the index storage 16 (S32). The searching part 17 searches an report ID linked commonly with the combination data kd that have different description unit data ws but have the same diagnosed disease name word wd, by using the searched combination data Kd as a parameter (S33).

When the commonly linked report ID is specified, the searching part 17 specifies the search results by flagging the combination data kd linked with the report ID as a result of the search (S34). The counter 19 counts the number of the combination data kd including the same diagnosed disease name word wd for every diagnosed disease name word wd by using the flagged combination data kd as a parameter (S35).

After the search by the searching part 17 and the counting by the counter 19, the list generator 18 generates a list in which each diagnosed disease name word wd included in the combination data kd flagged by the searching part 17 is linked with the counted number (S36). Then, the list generator 18 sends the generated list to the interpretation terminal 2 via the input/output part 11 and the network N, (S37). Upon receipt of a command to request a list of radiology reports that further include the selected diagnosed disease name word wd (S38), the list generator 18 searches in the report database 12a by using the report IDs flagged and linked with the combination data kd including the selected diagnosed disease name word wd as a search key, and acquires records of the relevant radiology reports (S39). Subsequently, the list generator generates a list in which the records of the radiology reports are listed, and send to the interpretation terminal 2 via the input/output part 11 and the network N (S40). Upon receipt of a command to request the selected radiology reports (S41), the report transmission/receiving controller 12 searches in the report database 12a by using a report ID included in the command (S42), reads out radiology reports from an archive area of the archive 10 indicated via a path recorded in the relevant record (S43), and sends them to the interpretation terminal 2 via the input/output part 11 and the network N (S44). In the interpretation terminal 2, the received radiology reports are displayed on the monitor 22 by the previous-report display controller 26.

Thus, in the report searching apparatus 1 according to the present embodiment, by previously generating, as indexes, such data that links report IDs with combination data kd combining words in the finding field Cs such as word-sets of description units included in the radiology reports with words in the diagnosed disease name field Ck are linked with, the operator can know words in the diagnosed disease name field Ck that are closely related to all of the description units in the diagnosed disease name field Ck inputted by himself/herself, and can further narrow them down to the desired radiology reports by using the words in the diagnosed disease name field Ck. Furthermore, because the number of radiology reports that include all of the inputted description units and the words in the diagnosed disease name field Ck is displayed in the list of words in the diagnosed disease name field Ck, this number becomes the degree of relevance between the words in the finding field Cs inputted by himself/herself and the words in the diagnosed disease name field Ck, with the result that it is possible to narrow down to radiology reports with high referential value.

Next, another example of combination data kd in which a plurality of sentences are included in the finding field Cs of radiology reports, and another search example with combination data kd will be explained.

Figure 17:
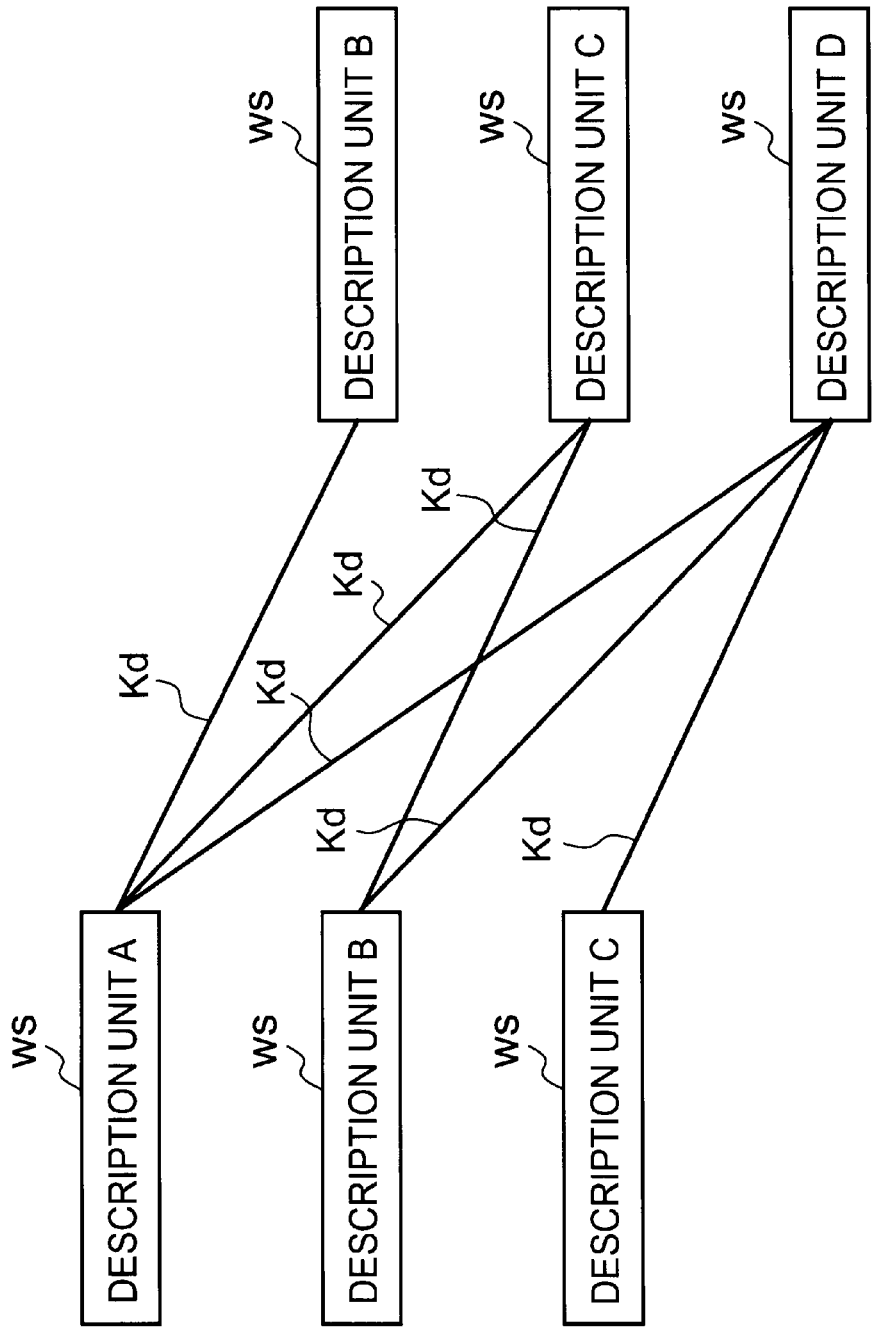
FIG. 17 shows another example of indexes stored in the index storage.

FIG. 17 is a data configuration view showing another example of indexes stored in the index storage 16. The index storage 16 stores combination data Kd of description unit data ws written in the finding field Cs of the same radiology report. For example, if sentences A, B, C and D are written in the finding field Cs of the radiology report A, description unit data ws of A, B, C and D are created by structuring the sentences A, B, C and D from this radiology report A, and six kinds of combination data Kd in total are generated and stored into the index storage 16. The six kinds of combination data Kd are formed by combining two of the description unit data ws.

Figure 18:
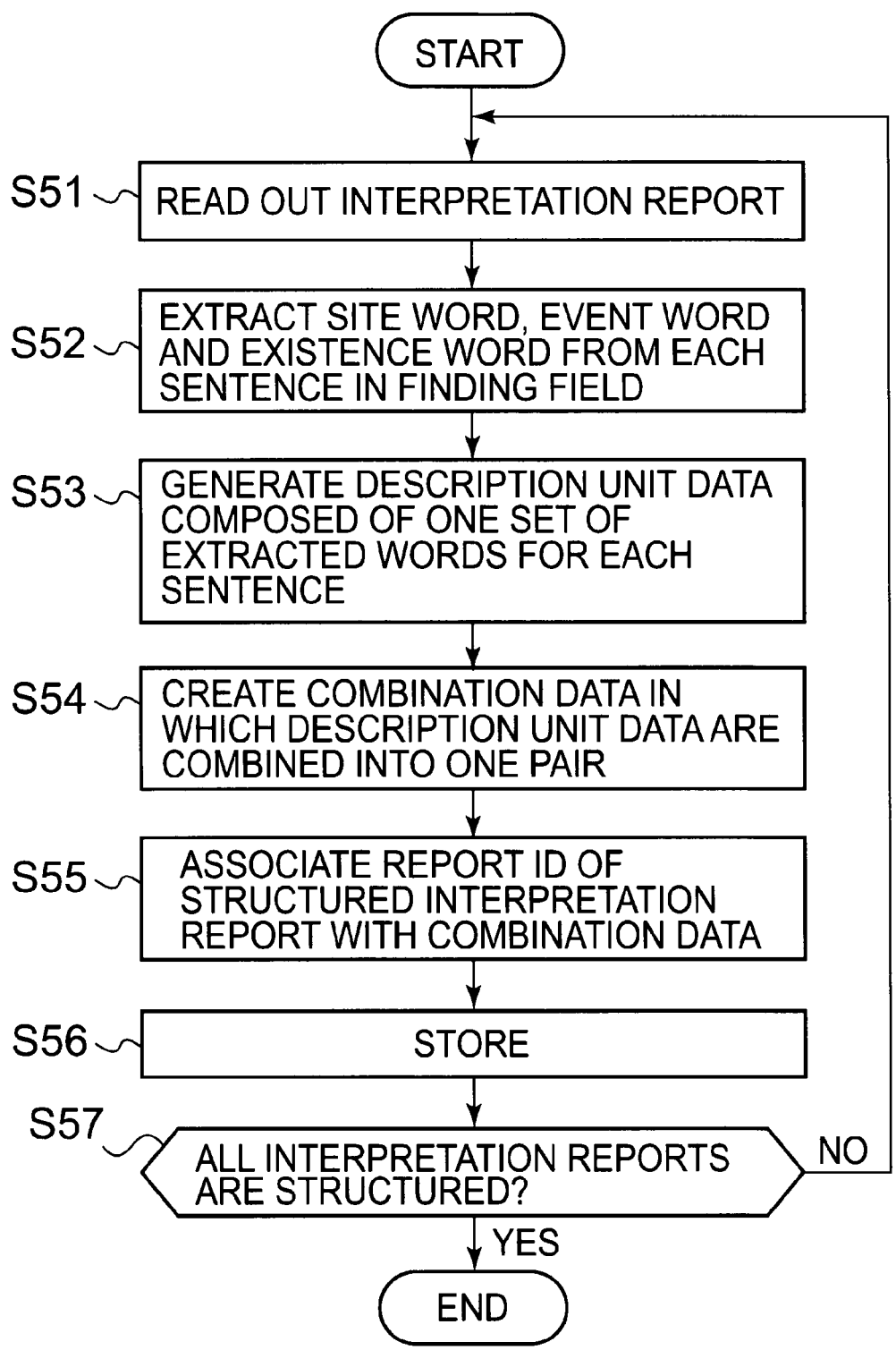
FIG. 18 is a flowchart showing an example of a process for creating combined data of a word with a word in a finding field as an index.

FIG. 18 is a flowchart showing an example of a process executed by the extraction part 13, dictionary storage 14 and combination generator 15, for creating combination data Kd of words in the finding filed as indexes. Firstly, the extraction part 13 reads out a radiology report from the archive 10 (S51).

Referring to the dictionary data, the extraction part 13 extracts the region word wb, the finding word wj, and the confidence word wu for every sentence from the finding field Cs of the read-out radiology report (S52), and creates description unit data ws, in which words extracted from one sentence form one set, for every sentence (S53).

Subsequently, the combination generator 15 creates combination data Kd in which one of the description unit data ws is combined with another (S54). Then, when the combination data Kd is created, the combination generator 15 links a report ID for identifying a structured radiology report with the combination data Kd (S55), and stores it in the index storage 16 (S56). Then, if all of the radiology reports stored in the index storage 16 are not restructured (S57, No), the following radiology report repeats steps S51 to S56.

Figure 19:
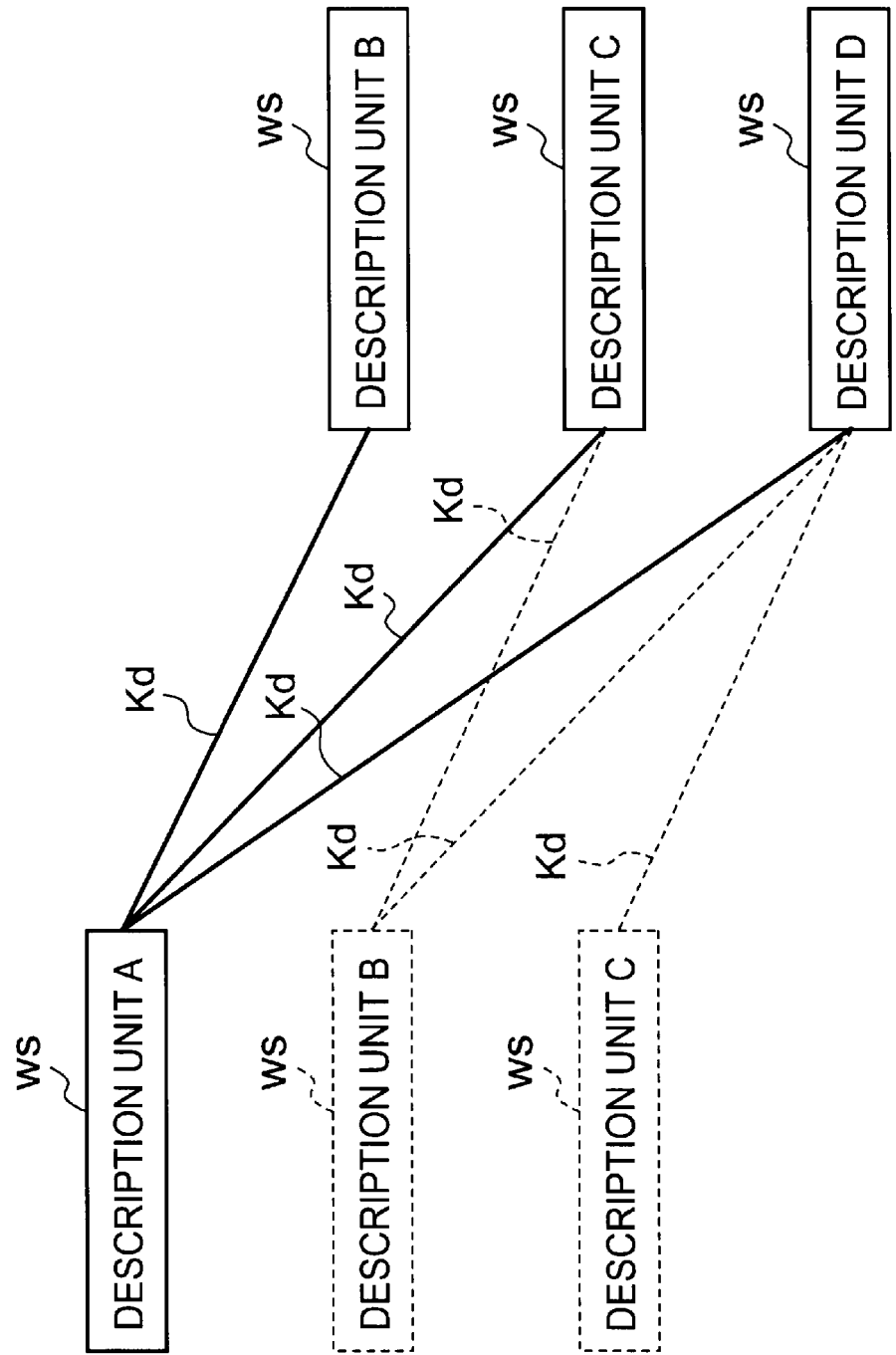
FIG. 19 shows a search example when combined data of words in the finding field is stored as an index.

FIG. 19 is a schematic view showing a search example in which the combination data Kd is inputted as an index. For example, when a description unit data ws of A is inputted by using the operating part 23, the searching part 17 specifies the combination data KdA, KdC including this description unit data ws. When the searching part 17 specifies the combination data kdA, KdC, the counter 19 counts the numbers of the combination data kdA and combination data kdC.

Subsequently, the list generator 18 generates a list in which the other description unit data ws of B and description unit data ws of C included in these combination data kdA, KdC are listed, and sends it to the interpretation terminal 2.

The sent list is displayed in the search-results field SLf on the search screen of the monitor 22 provided in the interpretation terminal.

Thus, in the report searching apparatus 1 according to the present embodiment, each combination data Kd combining two data among a plurality of description units included in the radiology report, is previously generated as an index. Accordingly, the operator can know the findings that are closely related to the findings inputted by himself/herself, and can further narrow down to desired radiology reports.

It should be noted that, in the respective embodiments, a typical word that represents a certain meaning may be correlated with a word having the same meaning as the typical word in the dictionary data.

Then, after scanning of sentences and matching of words, the extraction part 13 extracts a typical word of the matched word, instead of an actually matched word. Further, referring to dictionary data stored in the dictionary storage 14, the searching part 17 converts a word included in a search key to a typical word.

Consequently, the searching part 17 can specify combination data including a word that does not completely match the word inputted by using the operating part 23 for search but has the same meaning, whereby it is possible to reduce variation of search results due to mistakes in selecting a search word. Moreover, the counting result produced by the counter 19 may have less variety, depending on differences in words.

For classification of the confidence word Wu, other than words with an affirmative meaning such as "positive" or "negative," words with the meaning of a predetermined level of certainty such as "suspected" may be included.

Figure 20:
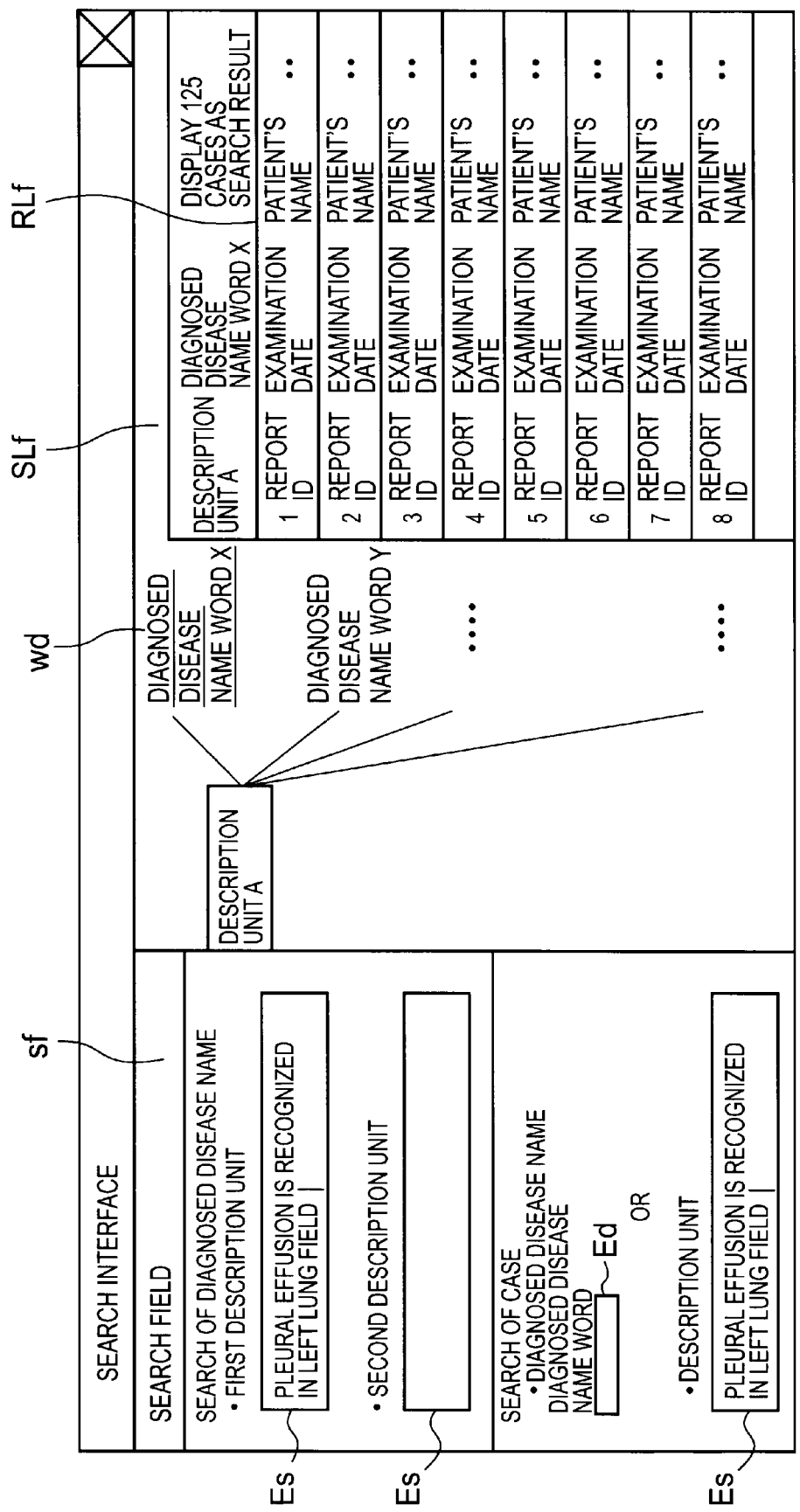
FIG. 20 shows another example of a search screen.

In the respective embodiments, each of the words composing the description unit data ws is inputted as a search key. However, as shown in FIG. 20, a sentence indicating a finding may be inputted as a search key. In the search screen, a sentence that includes the region word wb, finding word wj and confidence word wu is inputted in the field Es for inputting a search key, and the inputted sentence is sent to the report searching apparatus 1. In this case, the searching part 17 refers to the dictionary data stored in the dictionary storage 14, decomposes the inputted sentence into words, and extracts the region word wb, finding word wj and confidence word wu. Then, the extracted region word wb, finding word wj and the confidence word wu are used as description unit data ws to search the combination data kd.

The counting by the counter 19 may be performed in a previously set counting period, instead of in the searching phase.

As described above, according to the report searching apparatus 1 and the method for searching the report in the respective embodiments, the operator can check words closely related to the words inputted by himself/herself, and can further narrow down to desired radiology reports by using the words.

Consequently, this can reduce the time needed to check the contents of the radiology reports and to search the desired radiology reports, in addition to improving the accuracy of searches. Furthermore, this makes it possible to easily examine other possibilities in judging the interpretation without overlooking, by exhibiting words closely related to the words inputted by himself/herself. Moreover, the relation of the typical diagnosed disease names to the findings or typical findings to the diagnosed disease names is reviewed, so that this may be used for education.

What is claimed is:

1. A report searching apparatus, comprising:
    an archive configured to archive a plurality of radiology reports;
    an extracting part configured to extract specified types of words from the plurality of radiology reports;
    a combination generator configured to generate combinations of words extracted from the radiology reports, for every radiology report;
    an index storage configured to store the combinations generated by the combination generator;
    a searching part configured to, in response to an input operation of inputting the specified types of words, search the combinations each including the inputted specified types of words as one part thereof, from the index storage;
    a list generator configured to generate a list of the other part of the specified types of words included in each of the combinations searched by the searching part and, in response to an input operation of selecting any word from the list of the words, generate a list of radiology reports including the one word having been inputted and the other word having been selected; and an output part configured to, in response to an input operation of selecting any report from the list of the radiology reports, output a selected radiology report from the archive, wherein the extracting part includes a dictionary storage configured to store dictionary data including a word in a finding field and a word in a diagnosed disease name field of a radiology report, and extracts the word in the finding field and the word in the diagnosed disease name field included in the dictionary data, and wherein the combination generator generates a combination of the word in the finding field and the word in the diagnosed disease name field.

2. The report searching apparatus according to claim 1, wherein:

the index storage stores so that the combinations are linked with information identifying radiology reports including the combinations; and the searching part, in response to an input operation of inputting a plurality of words, searches the combinations including any of the inputted words and linked with information identifying the same radiology report, from the index storage.

3. The report searching apparatus according to claim 1, further comprising:

a counter configured to count the number of the combinations including the same other word, from among the combinations searched by the searching part, wherein:

the list generator creates a list in which the other word is linked with the number of the combinations including the other word.

4. The report searching apparatus according to claim 1, wherein:

the extracting part includes a dictionary storage configured to store dictionary data including words in the finding field of the radiology report, and extracts the word in the finding field included in the dictionary data; and the combination generator generates a combination of the words in the finding field.

5. The report searching apparatus according to claim 4, wherein:

the dictionary storage stores the dictionary data including words indicating regions, words indicating findings occurring at the regions, and words indicating positive/negative of the findings;

the extracting part extracts the respective types of words included in one sentence as a set; and the combination generator generates the combination of a set of the respective types of words included in one sentence and a set of the respective types of words included in another sentence.

6. The report searching apparatus according to claim 1, wherein:

the dictionary storage stores the dictionary data including words indicating regions, words indicating findings occurring at the regions, and words indicating positive/negative of the findings, as words in the finding field;

the extracting part extracts the respective types of words included in one sentence as a set; and the combination generator generates the combination of the set and a word in the diagnosed disease name field.

7. The report searching apparatus according to claim 6, wherein:

the searching part, in response to an input operation of inputting a word-set, searches the combination including the inputted set, from the index storage.

8. The report searching apparatus according to claim 6, wherein:

the searching part, in response to an input operation of inputting one sentence, decomposes the inputted sentence into words, and searches the combination including a set of the decomposed words, from the index storage.

9. The report searching apparatus according to claim 1, wherein:

the searching part, in response to an input operation of inputting words in the finding field, searches the combination including the inputted words in the finding field, from the index storage.

10. The report searching apparatus according to claim 1, wherein:

the searching part, in response to an input operation of inputting words in the diagnosed disease name field, searches the combination including the inputted words in the diagnosed disease name field, from the index storage.

11. A report searching apparatus connected to a display configured to display a search screen directly or via a network, comprising:

an archive configured to archive a plurality of radiology reports;

a dictionary storage configured to store dictionary data including words in finding fields and words in diagnosed disease name fields of the radiology reports;

an extracting part configured to extract the words in the finding fields and the words in the diagnosed disease name fields included in the dictionary data, from the plurality of radiology reports;

a combination generator configured to generate combinations of the words in the finding fields and the words in the diagnosed disease name fields extracted from the radiology reports, for every radiology report;

an index storage configured to store the combinations generated by the combination generator;

a searching part configured to, in response to an input operation of inputting the words in the finding fields, search the combinations each including the inputted words as one part thereof, from the index storage;

a list generator configured to generate a list of the words in the diagnosed disease name fields included in the combinations searched by the searching part and, in response to an input operation of selecting any word from the list of the words in the diagnosed disease name fields, generate a list of radiology reports including the inputted word in the finding field and the selected word in the diagnosed disease name field; and an output part configured to first output the list of the words in the diagnosed disease name fields displayed on the search screen to the display, next output the list of the radiology reports displayed on the search screen to the display, and thereafter, in response to an input operation of selecting any report from the list of the radiology reports, output a selected radiology report from the archive to the display.

12. A method for searching a report in a report searching apparatus connected to an archive configured to archive a plurality of radiology reports, an operating part, and a display, the method comprising:

storing dictionary data including a word in a finding field and a word in a diagnosed disease name field of a radiology report;

extracting specified types of words from the plurality of radiology reports archived in the archive, and storing the words extracted from the radiology reports in combination, for every radiology report, wherein the extracting includes extracting the word in the finding field and the word in the diagnosed disease name field included in the dictionary data, and combining the word in the finding field and the word in the diagnosed disease name field;

in response to an input operation of inputting the specified types of words by using the operating part, searching the combinations including the inputted specified types of words as one part thereof, and generating a list of the other part of the specified types of words included in the searched combinations;

in response to an input operation of selecting any word from the list the words by using the operating part, generating a list of radiology reports including the one word having been inputted and the other word having been selected; and in response to an input operation of selecting any report from among the list of the radiology reports by using the operating part, outputting the selected radiology report from the archive to the display.

13. A method for searching a report in a report searching apparatus that is connected to an archive configured to archive a plurality of radiology reports, an operating part, and a display configured to display a search screen, and that has a dictionary storage configured to previously store dictionary data including words in finding fields and words in diagnosed disease name fields of the radiology reports, the method comprising:

extracting the words in the finding fields and the words in the diagnosed disease name fields included in the dictionary data from the plurality of radiology reports archived in the archive, and storing the words in the finding fields and the words in the diagnosed disease name fields extracted from the radiology reports in combination, for every radiology report;

in response to an input operation of inputting the words in the finding fields by using the operating part, searching the combinations including the inputted words as one part thereof, and generating a list of the words in the diagnosed disease name fields included in the searched combinations;

outputting the list of the words in the diagnosed disease name fields to the display;

in response to an input operation of selecting any word from the list of the words in the diagnosed disease name fields displayed on the search screen of the display by using the operating part, generating a list of radiology reports including the inputted words in the finding fields and the selected words in the diagnosed disease name fields;

outputting the list of the radiology reports to the display; and in response to an input operation of selecting any report from the list of the radiology reports displayed on the search screen of the display by using the operating part, outputting the selected radiology report from the archive to the display.

* * * * *